US012759018B2

(12) United States Patent
Chen et al.

(10) Patent No.: US 12,759,018 B2
(45) Date of Patent: Oct. 13, 2026

(54) SURFACE MODIFICATION IN THE VAPOR PHASE

(71) Applicant: Quantum-Si Incorporated, Guilford, CT (US)

(72) Inventors: Guojun Chen, Sherborn, MA (US); Jeremy Lackey, Foster City, CA (US)

(73) Assignee: Quantum-Si Incorporated, Branford, CT (US)

( * ) Notice: Subject to any disclaimer, the term of this patent is extended or adjusted under 35 U.S.C. 154(b) by 0 days.

(21) Appl. No.: 18/333,880

(22) Filed: Jun. 13, 2023

(65) Prior Publication Data

US 2024/0157395 A1 May 16, 2024

Related U.S. Application Data

(63) Continuation of application No. 17/067,184, filed on Oct. 9, 2020, now Pat. No. 11,712,715.

(60) Provisional application No. 62/914,356, filed on Oct. 11, 2019.

(51) Int. Cl.

| | |
|---|---|
| ***C23C 24/10*** | (2006.01) |
| ***B05D 1/00*** | (2006.01) |
| ***B05D 3/10*** | (2006.01) |
| ***G01N 33/543*** | (2006.01) |

(52) U.S. Cl.

CPC ............... *B05D 1/60* (2013.01); *B05D 3/104* (2013.01); *G01N 33/54306* (2013.01); *G01N 33/54366* (2013.01); *B05D 2203/30* (2013.01); *B05D 2350/60* (2013.01)

(58) Field of Classification Search

CPC ...... B05D 1/60; B05D 3/104; B05D 2203/30; B05D 2350/60

See application file for complete search history.

(56) References Cited

U.S. PATENT DOCUMENTS

| | | | |
|---|---|---|---|
| 4,659,481 | A | 4/1987 | Chen |
| 5,106,730 | A | 4/1992 | Van Ness et al. |
| 5,185,243 | A | 2/1993 | Ullman et al. |
| 5,194,370 | A | 3/1993 | Berninger et al. |
| 5,707,804 | A | 1/1998 | Mathies et al. |
| 5,851,840 | A | 12/1998 | Sluka et al. |

(Continued)

FOREIGN PATENT DOCUMENTS

| | | | |
|---|---|---|---|
| EP | 0 702 090 | A2 | 3/1996 |
| EP | 743 535 | A1 | 6/2014 |

(Continued)

OTHER PUBLICATIONS

Extended European Search Report for European Application No. 18794185.1 dated Jan. 11, 2021.

(Continued)

*Primary Examiner* — Dah-Wei D. Yuan
*Assistant Examiner* — Kristen A Dagenais
(74) *Attorney, Agent, or Firm* — Wolf, Greenfield & Sacks, P.C.

(57) ABSTRACT

Aspects of the application provide methods of producing substrates having modified surfaces. In some aspects, methods of surface modification involve treating a surface of a substrate with an organic reagent in vapor phase to form an organic layer over the surface. In some aspects, methods of forming a stable surface coating on an oxidized surface are provided.

21 Claims, 9 Drawing Sheets

(56) References Cited

U.S. PATENT DOCUMENTS

| | | | |
|---|---|---|---|
| 6,153,442 | A | 11/2000 | Pirio et al. |
| 6,248,518 | B1 | 6/2001 | Parkhurst et al. |
| 6,255,083 | B1 | 7/2001 | Williams |
| 6,264,825 | B1 | 7/2001 | Blackburn et al. |
| 6,429,258 | B1 | 8/2002 | Morgan et al. |
| 6,517,776 | B1 | 2/2003 | Rodgers et al. |
| 6,762,048 | B2 | 7/2004 | Williams |
| 6,787,308 | B2 | 9/2004 | Balasubramanian et al. |
| 6,846,638 | B2 | 1/2005 | Shipwash |
| 6,869,764 | B2 | 3/2005 | Williams et al. |
| 6,936,702 | B2 | 8/2005 | Williams et al. |
| 7,052,847 | B2 | 5/2006 | Korlach et al. |
| 7,056,661 | B2 | 6/2006 | Korlach et al. |
| 7,229,799 | B2 | 6/2007 | Williams |
| 7,361,466 | B2 | 4/2008 | Korlach et al. |
| 7,399,590 | B2 | 7/2008 | Piepenburg et al. |
| 7,442,412 | B2 | 10/2008 | Miller |
| 7,928,038 | B2 | 4/2011 | Menchen et al. |
| 7,968,702 | B2 | 6/2011 | Wegener et al. |
| 8,034,623 | B2 | 10/2011 | Oh et al. |
| 8,084,734 | B2 | 12/2011 | Vertes et al. |
| 8,153,375 | B2 | 4/2012 | Travers et al. |
| 8,173,198 | B2 | 5/2012 | Menchen et al. |
| 8,192,961 | B2 | 6/2012 | Williams |
| 8,252,910 | B2 | 8/2012 | Korlach et al. |
| 8,257,954 | B2 | 9/2012 | Clark et al. |
| 8,309,330 | B2 | 11/2012 | Travers et al. |
| 8,354,252 | B2 | 1/2013 | Wegener et al. |
| 8,420,366 | B2 | 4/2013 | Clark et al. |
| 8,455,193 | B2 | 6/2013 | Travers et al. |
| 8,501,406 | B1 | 8/2013 | Gray et al. |
| 8,530,154 | B2 | 9/2013 | Williams |
| 8,581,179 | B2 | 11/2013 | Franzen |
| 8,846,881 | B2 | 9/2014 | Korlach et al. |
| 8,906,614 | B2 | 12/2014 | Wegener et al. |
| 8,927,212 | B2 | 1/2015 | Kong et al. |
| 8,980,584 | B2 | 3/2015 | Williams |
| 9,062,091 | B2 | 6/2015 | Bjornson et al. |
| 9,404,146 | B2 | 8/2016 | Travers et al. |
| 9,435,810 | B2 | 9/2016 | Havranek et al. |
| 9,464,107 | B2 | 10/2016 | Wegener et al. |
| 9,542,527 | B2 | 1/2017 | Travers et al. |
| 9,551,031 | B2 | 1/2017 | Korlach et al. |
| 9,551,660 | B2 | 1/2017 | Kong et al. |
| 9,566,335 | B1 | 2/2017 | Emili et al. |
| 9,582,640 | B2 | 2/2017 | Travers et al. |
| 9,600,626 | B2 | 3/2017 | Travers et al. |
| 9,606,058 | B2 | 3/2017 | Rothberg et al. |
| 9,617,594 | B2 | 4/2017 | Rothberg et al. |
| 9,678,012 | B2 | 6/2017 | Rothberg et al. |
| 9,678,080 | B2 | 6/2017 | Bjornson et al. |
| 9,696,258 | B2 | 7/2017 | Rothberg et al. |
| 9,719,073 | B2 | 8/2017 | Emig et al. |
| 9,759,658 | B2 | 9/2017 | Rothberg et al. |
| 9,784,679 | B2 | 10/2017 | Rothberg et al. |
| 9,845,501 | B2 | 12/2017 | Williams |
| 9,863,880 | B2 | 1/2018 | Rothberg et al. |
| 9,879,319 | B2 | 1/2018 | Korlach et al. |
| 9,910,956 | B2 | 3/2018 | Travers et al. |
| 9,921,157 | B2 | 3/2018 | Rothberg et al. |
| 9,957,291 | B2 | 5/2018 | Sebo et al. |
| 9,983,135 | B2 | 5/2018 | Rothberg et al. |
| 10,023,605 | B2 | 7/2018 | Bjornson et al. |
| 10,048,208 | B2 | 8/2018 | Rothberg et al. |
| 10,066,258 | B2 | 9/2018 | Kong et al. |
| 10,150,872 | B2 | 12/2018 | Zheng et al. |
| 10,161,002 | B2 | 12/2018 | Korlach et al. |
| 10,174,363 | B2 | 1/2019 | Rothberg et al. |
| 10,481,162 | B2 | 11/2019 | Emili et al. |
| 10,544,449 | B2 | 1/2020 | Shen et al. |
| 10,545,153 | B2 | 1/2020 | Marcotte et al. |
| 10,570,445 | B2 | 2/2020 | Kong et al. |
| 10,676,788 | B2 | 6/2020 | Shen et al. |
| 10,731,209 | B2 | 8/2020 | Ball et al. |
| 10,745,750 | B2 | 8/2020 | Korlach et al. |
| 10,787,573 | B2 | 9/2020 | Zheng et al. |
| 11,224,878 | B2 | 1/2022 | Rothberg et al. |
| 11,712,715 | B2 | 8/2023 | Chen et al. |
| 12,528,083 | B2 | 1/2026 | Rothberg et al. |
| 2002/0128234 | A1 | 9/2002 | Hubbell et al. |
| 2003/0077452 | A1 | 4/2003 | Guire et al. |
| 2004/0009300 | A1 | 1/2004 | Shimakura et al. |
| 2005/0042633 | A1 | 2/2005 | Williams |
| 2005/0266456 | A1 | 12/2005 | Williams et al. |
| 2005/0277780 | A1 | 12/2005 | Gordon et al. |
| 2006/0173497 | A1 | 8/2006 | Mech et al. |
| 2006/0234901 | A1 | 10/2006 | Scheuing et al. |
| 2007/0072196 | A1 | 3/2007 | Xu et al. |
| 2007/0197890 | A1 | 8/2007 | Boock et al. |
| 2007/0219367 | A1 | 9/2007 | Shchepinov et al. |
| 2008/0032301 | A1 | 2/2008 | Rank et al. |
| 2008/0050747 | A1 | 2/2008 | Korlach et al. |
| 2008/0241512 | A1 | 10/2008 | Boris et al. |
| 2008/0280142 | A1 | 11/2008 | Birmingham et al. |
| 2009/0263802 | A1 | 10/2009 | Drmanac |
| 2010/0009872 | A1 | 1/2010 | Eid et al. |
| 2010/0029494 | A1 | 2/2010 | Cherkasov et al. |
| 2010/0035254 | A1 | 2/2010 | Williams |
| 2011/0003343 | A1 | 1/2011 | Nikiforov et al. |
| 2011/0250626 | A1 | 10/2011 | Williams et al. |
| 2011/0281776 | A1 | 11/2011 | Eshoo et al. |
| 2012/0178165 | A1 | 7/2012 | Meagher et al. |
| 2012/0322692 | A1 | 12/2012 | Pham et al. |
| 2013/0116153 | A1 | 5/2013 | Bowen et al. |
| 2013/0296195 | A1* | 11/2013 | Gray .................... B01J 19/0046 506/18 |
| 2013/0316912 | A1 | 11/2013 | Bjornson et al. |
| 2014/0093935 | A1 | 4/2014 | Shen |
| 2015/0141267 | A1 | 5/2015 | Rothberg et al. |
| 2015/0141268 | A1 | 5/2015 | Rothberg et al. |
| 2015/0177150 | A1 | 6/2015 | Rothberg et al. |
| 2015/0280020 | A1 | 10/2015 | Kärkkäinen et al. |
| 2015/0299848 | A1 | 10/2015 | Haukka et al. |
| 2016/0041095 | A1 | 2/2016 | Rothberg et al. |
| 2016/0133668 | A1 | 5/2016 | Rothberg et al. |
| 2016/0341664 | A1 | 11/2016 | Rothberg et al. |
| 2016/0344156 | A1 | 11/2016 | Rothberg et al. |
| 2016/0369332 | A1 | 12/2016 | Rothberg et al. |
| 2016/0370291 | A1 | 12/2016 | Rothberg et al. |
| 2016/0370292 | A1 | 12/2016 | Rothberg et al. |
| 2016/0377543 | A1 | 12/2016 | Rothberg et al. |
| 2016/0380025 | A1 | 12/2016 | Rothberg et al. |
| 2017/0107562 | A1 | 4/2017 | Rothberg et al. |
| 2017/0136433 | A1 | 5/2017 | Sun et al. |
| 2017/0349944 | A1 | 12/2017 | Rothberg et al. |
| 2017/0350818 | A1 | 12/2017 | Rothberg et al. |
| 2017/0362651 | A1 | 12/2017 | Rothberg et al. |
| 2018/0127809 | A1 | 5/2018 | Andruzzi et al. |
| 2018/0163312 | A1* | 6/2018 | Blomberg .............. C09K 13/08 |
| 2018/0208911 | A1 | 7/2018 | Reed et al. |
| 2018/0211003 | A1 | 7/2018 | Travers et al. |
| 2018/0217092 | A1 | 8/2018 | Hinz et al. |
| 2018/0223353 | A1 | 8/2018 | Ball et al. |
| 2018/0299460 | A1 | 10/2018 | Emili |
| 2018/0326412 | A1 | 11/2018 | Rothberg et al. |
| 2018/0346507 | A1 | 12/2018 | Sebo et al. |
| 2019/0010183 | A1 | 1/2019 | Bjornson et al. |
| 2019/0017170 | A1 | 1/2019 | Sharma et al. |
| 2019/0249153 | A1 | 8/2019 | Kamtekar et al. |
| 2020/0141944 | A1 | 5/2020 | Emili et al. |
| 2020/0148727 | A1 | 5/2020 | Tullman et al. |
| 2020/0190575 | A1 | 6/2020 | Tsay et al. |
| 2020/0219590 | A1 | 7/2020 | Reed et al. |
| 2021/0129179 | A1 | 5/2021 | Chen et al. |
| 2022/0098658 | A1 | 3/2022 | Chen et al. |
| 2022/0305487 | A1 | 9/2022 | Rothberg et al. |
| 2024/0409995 | A1* | 12/2024 | Estandian .......... G01N 21/6486 |

FOREIGN PATENT DOCUMENTS

| | | | |
|---|---|---|---|
| JP | S57-35678 | A | 2/1982 |
| JP | H04-154792 | A | 5/1992 |
| JP | 2003-077699 | A | 3/2003 |
| JP | 2004-527651 | A | 9/2004 |

(56) References Cited

FOREIGN PATENT DOCUMENTS

| | | | | |
|---|---|---|---|---|
| KR | 10-0814980 | B1 | 3/2008 | |
| KR | 2019-0093593 | A | 8/2019 | |
| WO | WO 1996/21036 | A2 | 7/1996 | |
| WO | WO 2005/044836 | A2 | 5/2005 | |
| WO | WO 2005/093870 | A1 | 10/2005 | |
| WO | WO 2007/070572 | A2 | 6/2007 | |
| WO | WO 2007/075987 | A2 | 7/2007 | |
| WO | WO 2010/065322 | A1 | 6/2010 | |
| WO | WO 2010/115016 | A2 | 10/2010 | |
| WO | WO 2011/049816 | A2 | 4/2011 | |
| WO | WO 2012/024500 | A1 | 2/2012 | |
| WO | WO 2013/158982 | A1 | 10/2013 | |
| WO | WO 2014/195271 | A1 | 12/2014 | |
| WO | WO 2015/038954 | A1 | 3/2015 | |
| WO | WO 2016/187580 | A1 | 11/2016 | |
| WO | WO 2017/201514 | A1 | 11/2017 | |
| WO | WO 2018/106955 | A1 | 6/2018 | |
| WO | WO 2018/118992 | A1 | 6/2018 | |
| WO | WO 2018/154572 | A1 | 8/2018 | |
| WO | WO 2018/170382 | A1 | 9/2018 | |
| WO | WO-2018204810 | A1 * | 11/2018 | ........... C09D 171/02 |
| WO | WO 2019/040825 | A1 | 2/2019 | |
| WO | WO 2020/102741 | A1 | 5/2020 | |

OTHER PUBLICATIONS

International Search Report and Written Opinion for International Application No. PCT/US2018/031125 dated Jul. 9, 2018.
International Preliminary Report on Patentability for International Application No. PCT/US2018/031125 dated Nov. 14, 2019.
International Search Report and Written Opinion for International Application No. PCT/US2017/067421 dated Mar. 6, 2018.
International Preliminary Report on Patentability for International Application No. PCT/US2017/067421 dated Jul. 4, 2019.
Invitation to Pay Additional Fees for Application No. PCT/US2020/055052 mailed on Feb. 4, 2021.
International Search Report and Written Opinion for International Application No. PCT/US2020/055052 dated Mar. 26, 2021.
International Preliminary Report on Patentability for International Application No. PCT/US2020/055052 mailed on Apr. 21, 2022.
International Search Report and Written Opinion for International Application No. PCT/US2021/051371 dated Dec. 27, 2021.
International Preliminary Report on Patentability for International Application No. PCT/US2021/051371 dated Mar. 30, 2023.
[No Author Listed] Compound Summary: Phenyl Dichlorophosphate. PubChem: https://pubchem.ncbi.nlm.nih.gov/compound/Phenyl-dichlorophosphate. Created Mar. 26, 2005. Modified Nov. 20, 2021. Last Accessed Nov. 27, 2021, 33 pages.
[No Author Listed] Poloxamer 407. Retrieved from the internet <https://en.wikipedia.org/wiki/Poloxamer_407> last edited Nov. 5, 2019. 1pg.
Heller, DNA Microarray Technology: Devices, Systems and Applications. Annu Rev Biomed Eng. 2002;4:129-53. Epub Mar. 22, 2002.
Huang et al., Biotin-derivatized poly (L-lysine)-g-poly (ethylene glycol): A novel polymeric interface for bioaffinity sensing. Langmuir. Jan. 8, 2002;18(1):220-30.
Koushik et al., Cerulean, Venus, and VenusY67C FRET reference standards. Biophys J. Dec. 15, 2006;91(12):L99-L101. doi: 10.1529/biophysj.106.096206. Epub Oct. 13, 2006. PMID: 17040988; PMCID: PMC1779932.
Nwe et al., Growing applications of "click chemistry" for bioconjugation in contemporary biomedical research. Cancer Biother Radiopharm. Jun. 2009;24(3):289-302. doi: 10.1089/cbr.2008.0626.
Saito et al., Dual-labeled oligonucleotide probe for sensing adenosine via FRET: a novel alternative to SNPs genotyping. Chem Commun (Camb). Jun. 7, 2007;(21):2133-5. doi: 10.1039/b618465k. Epub Feb. 28, 2007. PMID: 17520113.
Sato et al., Polyproline-rod approach to isolating protein targets of bioactive small molecules: isolation of a new target of indomethacin. J Am Chem Soc. Jan. 31, 2007;129(4):873-80. doi: 10.1021/ja0655643. PMID: 17243824.
Stryer et al., Energy transfer: a spectroscopic ruler. Proc Natl Acad Sci U S A. Aug. 1967;58(2):719-26. doi: 10.1073/pnas.58.2.719. PMID: 5233469; PMCID: PMC335693.
Thirumurugan et al., Click chemistry for drug development and diverse chemical-biology applications. Chem Rev. Jul. 10, 2013;113(7):4905-79. doi: 10.1021/cr200409f. Epub Mar. 27, 2013.
Tuske et al., The J-helix of Escherichia coli DNA polymerase I (Klenow fragment) regulates polymerase and 3'-5'-exonuclease functions. J Biol Chem. Aug. 4, 2000;275(31):23759-68.
Williams et al., An artificial processivity clamp made with streptavidin facilitates oriented attachment of polymerase-DNA complexes to surfaces. Nucleic Acids Res. Oct. 2008;36(18):e121. doi: 10.1093/nar/gkn531. Epub Aug. 22, 2008. PMID: 18723573; PMCID: PMC2566871.
Extended European Search Report for European Application No. 21870429.4 dated Jul. 30, 2024.
Fijen et al., A single-molecule FRET sensor for monitoring DNA synthesis in real time. Physical Chemistry Chemical Physics. 2017;19(6):4222-30.
Swaminathan, Single molecule peptide sequencing (Doctoral dissertation). The University of Texas at Austin. May 2015. 127 pages.
Balaji et al., Influence of laser power on POC13 diffused back surface field on n-type PERT silicon solar cells with local back contact. Current Applied Physics. Sep. 1, 2013;13(7):1397-400.
Verbelen et al., Selective substitution of POC13 with organometallic reagents: Synthesis of phosphinates and phosphonates. Synthesis. May 2018;50(10):2019-26.

* cited by examiner

Atomic Concentration (%) Determined by High Resolution Spectra

| | C1s | N1s | O1s | F1s | Si2p | Cl2p | K2p | Ti2p | Fe2p3 |
|---|---|---|---|---|---|---|---|---|---|
| Control | 17.8 | 2.5 | 58.5 | 0.4 | 13.5 | 0.0 | 0.0 | 7.4 | 0.0 |
| Soak in TFA | 20.0 | 1.8 | 58.0 | 0.0 | 12.9 | 0.1 | 0.0 | 7.0 | 0.2 |

$SiO_2$ Surface

| | C2H5O | Si | CN | CNO | PO2 | SiO3 |
|---|---|---|---|---|---|---|
| Blank Control ($SiO_2$) | 9649 | 634448 | 5152 | 865 | 9116 | 40816 |
| Sample 1 ($SiO_2$ +HPA) | 178442 | 161457 | 29898 | 16051 | 6500 | 21508 |
| Sample 2 ($SiO_2$ +HPA) | 175559 | 207084 | 26640 | 13877 | 6496 | 26090 |
| Sample 3 ($SiO_2$ -HPA) | 341863 | 75480 | 50180 | 32955 | 2202 | 17546 |
| Sample 4 ($SiO_2$ -HPA) | 336508 | 88409 | 45046 | 28152 | 2093 | 18655 |

$TiO_2$ Surface

| | | Ti | | | | TiO3 |
|---|---|---|---|---|---|---|
| Blank Control ($TiO_2$) | 25377 | 409097 | 21121 | 7814 | 4962 | 14500 |
| Sample 1 ($TiO_2$ +HPA) | 93884 | 340278 | 35257 | 24563 | 79327 | 5226 |
| Sample 2 ($TiO_2$ +HPA) | 79165 | 399789 | 31553 | 17042 | 86145 | 7639 |
| Sample 3 ($TiO_2$ -HPA) | 167349 | 348227 | 52653 | 30728 | 5948 | 8591 |
| Sample 4 ($TiO_2$ -HPA) | 220750 | 416953 | 59794 | 38547 | 4901 | 7660 |

*FIG. 8*

$$Selectivity = \frac{\alpha(\frac{I_{fragment}}{I_{Si}} - \frac{I_{fragment,control}}{I_{Si,control}})}{\beta(\frac{I_{fragment}}{I_{Ti}} - \frac{I_{fragment,control}}{I_{Ti,control}})};$$

$\alpha$: ionization sensitivity on SiO2 surface ;
$\beta$: ionization sensitivity on TiO2 surface;

| | C2H5O | Selectivity (SiO2/TiO2) | | |
|---|---|---|---|---|
| Blank Control ($SiO_2$) | 0.015208 | | | |
| Sample 1 ($SiO_2$ +HPA) | 1.105198 | 1.08999 | 5.096457 | (α/β) |
| Sample 2 ($SiO_2$ +HPA) | 0.847767 | 0.832559 | 6.12242 | (α/β) |
| Sample 3 ($SiO_2$ -HPA) | 4.529187 | 4.513978 | 10.78499 | (α/β) |
| Sample 4 ($SiO_2$ -HPA) | 3.806264 | 3.791056 | 8.110868 | (α/β) |
| | C2H5O | | | |
| Blank Control ($TiO_2$) | 0.062032 | | | |
| Sample 1 ($TiO_2$ +HPA) | 0.275904 | 0.213872 | | |
| Sample 2 ($TiO_2$ +HPA) | 0.198017 | 0.135985 | | |
| Sample 3 ($TiO_2$ -HPA) | 0.480574 | 0.418543 | | |
| Sample 4 ($TiO_2$ -HPA) | 0.529436 | 0.467404 | | |

| | CNO | Selectivity (SiO2/TiO2) | | |
|---|---|---|---|---|
| Blank Control ($SiO_2$) | 0.021193 | | | |
| Sample 1 ($SiO_2$ +HPA) | 0.74628 | 0.725088 | 0.174247 | (α/β) |
| Sample 2 ($SiO_2$ +HPA) | 0.53189 | 0.510697 | 0.301826 | (α/β) |
| Sample 3 ($SiO_2$ -HPA) | 1.878206 | 1.857013 | 0.611288 | (α/β) |
| Sample 4 ($SiO_2$ -HPA) | 1.509086 | 1.487893 | 0.331132 | (α/β) |
| | CNO | | | |
| Blank Control ($TiO_2$) | 0.538897 | | | |
| Sample 1 ($TiO_2$ +HPA) | 4.700153 | 4.161257 | | |
| Sample 2 ($TiO_2$ +HPA) | 2.23092 | 1.692024 | | |
| Sample 3 ($TiO_2$ -HPA) | 3.576766 | 3.03787 | | |
| Sample 4 ($TiO_2$ -HPA) | 5.032245 | 4.493349 | | |

| | CN | Selectivity (SiO2/TiO2) | | |
|---|---|---|---|---|
| Blank Control ($SiO_2$) | 0.126225 | | | |
| Sample 1 ($SiO_2$ +HPA) | 1.390087 | 1.263862 | 0.238923 | (α/β) |
| Sample 2 ($SiO_2$ +HPA) | 1.021081 | 0.894856 | 0.334664 | (α/β) |
| Sample 3 ($SiO_2$ -HPA) | 2.859911 | 2.733686 | 0.585092 | (α/β) |
| Sample 4 ($SiO_2$ -HPA) | 2.414688 | 2.288463 | 0.360423 | (α/β) |
| | CN | | | |
| Blank Control ($TiO_2$) | 1.456621 | | | |
| Sample 1 ($TiO_2$ +HPA) | 6.74646 | 5.289839 | | |
| Sample 2 ($TiO_2$ +HPA) | 4.130514 | 2.673894 | | |
| Sample 3 ($TiO_2$ -HPA) | 6.128856 | 4.672235 | | |
| Sample 4 ($TiO_2$ -HPA) | 7.806005 | 6.349385 | | |

*FIG. 9*

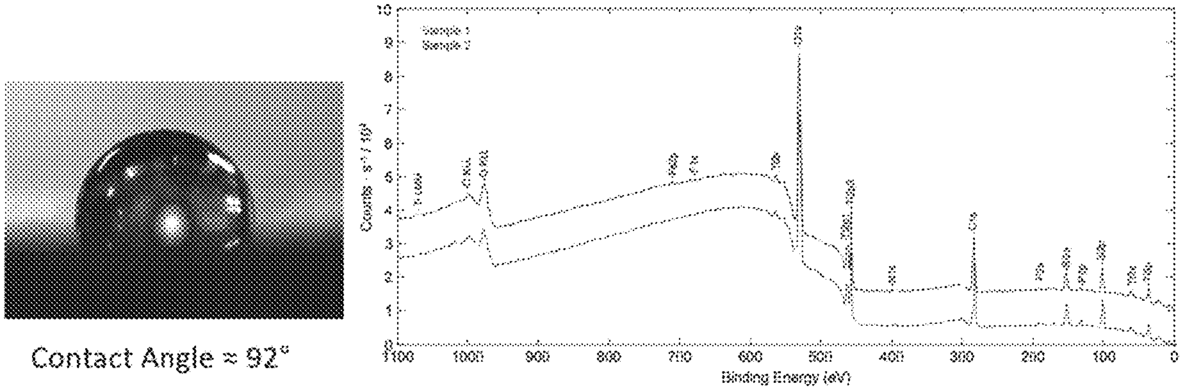
| C1s | N1s | O1s | F1s | Si2p | P2p | S2p | Cl2p | Ti2p |
|---|---|---|---|---|---|---|---|---|
| 20.4 | 2.8 | 54.3 | 0.2 | 10.1 | 1.0 | 0.3 | 0.2 | 10.7 |
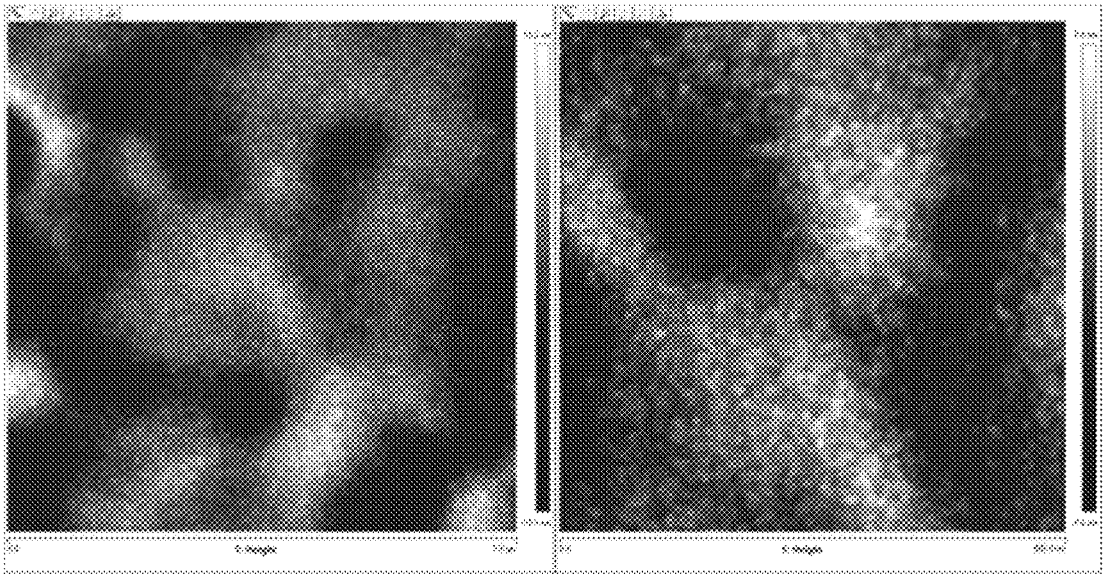
*FIG. 10*

SURFACE MODIFICATION IN THE VAPOR PHASE

RELATED APPLICATIONS

This application is a continuation of U.S. patent application Ser. No. 17/067,184, filed on Oct. 9, 2020, which claims priority to U.S. Provisional Application Ser. No. 62/914,356, filed Oct. 11, 2019, the entire contents of which is incorporated herein by reference.

BACKGROUND

Array-based platforms are widely used in massively parallel technologies for detecting and analyzing biomolecules. Examples of these platforms include microarrays used in biosensing and pixel arrays used in single molecule sequencing. Arrays generally include a collection of exceptionally small regions on the surface of a single device, with each region capable of independently assaying a sample. These regions can include selectively modified surface portions that are rendered to be more reactive or less reactive toward a desired chemical species. Certain assays require the use of corrosive solutions or other harsh conditions which can remove the desired surface functionality and/or damage the underlying material of the device surface.

SUMMARY

Aspects of the technology disclosed herein relate to methods of surface modification using one or more reagents in vapor phase. In some embodiments, the application relates to the use of vapor phase reagents in surface modification processes that conventionally use liquid phase reagents. In some aspects, the application provides methods of forming a phosphorus-containing layer on a substrate surface using a vapor phase reagent. In some embodiments, the application provides methods of forming a stable surface coating on a substrate surface. In some embodiments, the application provides methods of preparing a selectively modified portion of a substrate surface.

In some aspects, the application provides methods of forming a phosphorus-containing layer on a metallic surface. In some embodiments, the methods comprise treating a metallic surface with a phosphoryl halide in vapor phase, where the phosphoryl halide forms a phosphorus-containing layer on the metallic surface. In some embodiments, the methods further comprise treating the metallic surface with at least one chlorosilane in vapor phase, where the at least one chlorosilane forms a coating layer over the metallic surface. In certain embodiments, the at least one chlorosilane is a chlorosiloxane compound, an alkylchlorosilane compound, or both. In certain embodiments, the at least one chlorosilane is hexachlorodisiloxane, hexyltrichlorosilane, or both. In some embodiments, at least a portion of the coating layer is formed on the phosphorus-containing layer.

In some aspects, the application provides methods of modifying a surface of a substrate. In some embodiments, the methods comprise treating a substrate having a first surface portion and a second surface portion with a phosphoryl halide in vapor phase, where the phosphoryl halide preferentially forms a phosphorus-containing layer on the first surface portion. In some embodiments, the first and second surface portions have different surface properties. In some embodiments, the methods further comprise treating the substrate with at least one chlorosilane in vapor phase, where the at least one chlorosilane forms a coating layer over the first and second surface portions. In certain embodiments, the at least one chlorosilane is a chlorosiloxane compound, an alkylchlorosilane compound, or both. In certain embodiments, the at least one chlorosilane is hexachlorodisiloxane, hexyltrichlorosilane, or both. In certain embodiments, at least a portion of the coating layer is formed on the phosphorus-containing layer. In some embodiments, the methods further comprise, prior to treating the substrate with the phosphoryl halide in vapor phase, treating the substrate with a functionalizing agent that comprises a coupling moiety, where the functionalizing agent preferentially binds to the second surface portion, thereby functionalizing the second surface portion. In certain embodiments, the first surface portion is a metal or metal oxide surface. In certain particular embodiments, the first surface portion is a transitional metal oxide surface. In certain embodiments, the second surface portion is a transparent or glass surface. In certain embodiments, the second surface portion is a silica (SiO2) surface. In some embodiments, the first surface portion is a metallic or plastic surface, and the second surface portion is a transparent or glass surface (e.g., a silica surface).

In certain embodiments, the phosphoryl halide preferentially forms the phosphorus-containing layer on the first surface portion with about 2-fold to about 60-fold selectivity. In certain embodiments, the phosphoryl halide preferentially forms the phosphorus-containing layer on the first surface portion with about 4-fold to about 40-fold selectivity. In certain embodiments, the phosphoryl halide preferentially forms the phosphorus-containing layer on the first surface portion with about 8-fold to about 20-fold selectivity.

In some aspects, the application provides methods of functionalizing a sample well surface. In some embodiments, the methods comprise treating a sample well having a metal oxide surface and a silica surface with a functionalizing agent that comprises a coupling moiety. In some embodiments, the functionalizing agent preferentially binds to the silica surface, thereby functionalizing the sample well surface. In some embodiments, the methods further comprise treating the sample well with an organic reagent in vapor phase, where the organic reagent preferentially forms an organic layer on the metal oxide surface. In some embodiments, the organic reagent is a phosphoryl halide, and the organic layer is a phosphorus-containing layer. In some embodiments, the organic reagent is an organic phosphoryl halide, and the organic layer is an organophosphorus layer.

In some embodiments, the methods further comprise treating the sample well with one or more additional reagents that form a coating layer over the metal oxide and silica surfaces. In certain embodiments, the coating layer over the metal oxide surface is formed on side walls of the sample well and the coating layer over the silica surface is formed on a bottom surface of the sample well. In some embodiments, the one or more additional reagents are in vapor phase. In some embodiments, the one or more additional reagents are silanes, and the coating layer is a silane layer. In some embodiments, the one or more additional reagents are chlorosilanes. In some embodiments, the one or more of the additional reagents are hexachlorodisiloxane, hexyltrichlorosilane, or both. In some embodiments, the methods further comprise contacting the sample well with a molecule of interest that binds the coupling moiety, thereby coupling the molecule of interest to the sample well surface. In some embodiments, the molecule of interest is a biomolecule, such as a nucleic acid or a polypeptide. In certain embodiments, the polypeptide is a protein or fragment thereof. In certain particular embodiments, the coupled polypeptide is a substrate for polypeptide sequencing, i.e., the polypeptide itself is to be sequenced. Methods for sequencing and identifying proteins, polypeptides, and amino acids are disclosed in International Publication Number WO 2020/102741, which is incorporated herein by reference in its entirety. In certain embodiments, the polypeptide is a polymerizing enzyme. In certain particular embodiments, the polymerizing enzyme is a nucleic acid polymerase, e.g., for use in a nucleic acid sequencing reaction. In such nucleic acid sequencing reactions, the coupled polypeptide itself is not sequenced, and instead promotes the sequencing of a nucleic acid substrate. Methods for sequencing and identifying polynucleotides, nucleic acids, and nucleotides are disclosed in International Publication Number WO 2016/187580, which is incorporated herein by reference in its entirety.

Accordingly, in some aspects, the application provides methods of surface modification using a phosphoryl halide. In some embodiments, a phosphoryl halide of the application is of Formula (I):

(I)

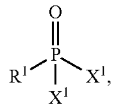

or a salt thereof, wherein: each instance of $X^1$ is independently a halogen; $R^1$ is optionally substituted alkyl, optionally substituted heteroalkyl, optionally substituted alkenyl, optionally substituted alkynyl, optionally substituted carbocyclyl, optionally substituted heterocyclyl, optionally substituted aryl, or optionally substituted heteroaryl, —$OR^O$, or —$N(R^N)_2$; each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group; or optionally two $R^O$ are taken together with the intervening atoms to form optionally substituted heterocyclyl; and each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are taken together with the intervening atoms to form optionally substituted heterocyclyl.

The details of certain embodiments of the invention are set forth herein. Other features, objects, and advantages of the invention will be apparent from the Detailed Description, Figures, Examples, and Claims.

BRIEF DESCRIPTION OF THE DRAWINGS

The accompanying drawings, which constitute a part of this specification, illustrate several embodiments of the invention and together with the description, serve to explain the principles of the invention.

FIG. 1A shows a workflow for preparing a selectively functionalized surface portion of a sample well. FIG. 1B shows a workflow for coating a sample well surface using a backfill process. FIG. 1C shows a workflow for coupling a molecule of interest to a functionalized surface.

FIG. 4A shows data obtained for surface coating formed by treatment with liquid phase hexylphosphonic acid. FIG. 4B shows data obtained for surface coating formed by treatment with vapor phase phosphonic dichloride.

FIG. 8 shows relative amounts of fragment peaks detected by TOF-SIMS for surface coatings on silica and titanium dioxide surfaces.

FIG. 9 shows selectivity calculations determined from the data shown in FIG. 8.

FIG. 10 shows imaging and spectra obtained during chemical and physical characterization of an array having modified surfaces.

DETAILED DESCRIPTION

Figure 1A:
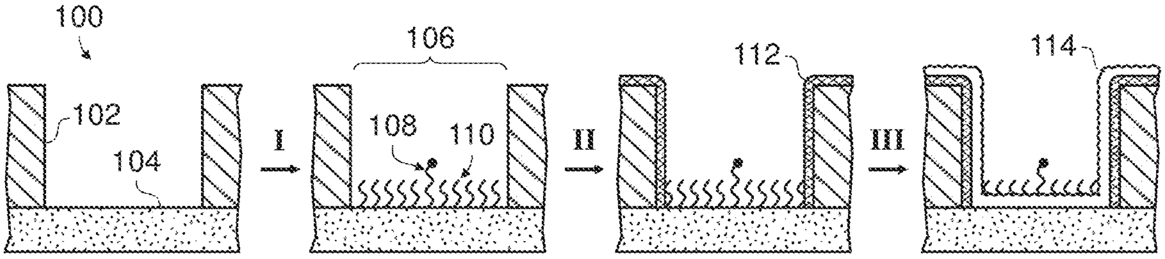
FIGS. 1A-1C show example workflows for surface modification in accordance with the application.

Aspects of the application relate to methods of using vapor phase reagents for preparing substrates having modified surfaces. In some aspects, the application provides methods of modifying a metallic or plastic surface of a substrate. In some embodiments, the substrate is treated with a phosphoryl halide in vapor phase to form a phosphorus-containing layer on the metallic or plastic surface of the substrate. In some embodiments, the substrate is treated with at least one silane to form a coating layer over the metallic or plastic surface of the substrate. In some embodiments, at least a portion of the coating layer is formed on the phosphorus-containing layer. In some aspects, the application provides methods of preparing selectively modified surface portions of a substrate, such as a sample well having surface portions with different surface properties.

In some aspects, the application relates to the discovery of surface modification techniques which may be used to modify the exposed surfaces of a substrate to enable selective surface functionalization and to confer anti-corrosive and/or antifouling properties on substrate surfaces, among other advantages. Previous techniques for forming a phosphorus-containing layer on a metallic or plastic surface involved the use of liquid phase reagents. The inventors have recognized and appreciated that phosphorus-containing layers can be formed using vapor phase reagents of the application which dramatically decrease preparation time and reduce chemical waste compared to previous liquid phase surface modification processes. The inventors have further recognized and appreciated that the use of such reagents minimizes liquid-associated process steps which advantageously improves scalability of the overall process and coating consistency and uniformity.

In some aspects, the application relates to the discovery of stable surface coatings which can render a substrate, such as an array, biosensor, or other assay device, more capable of withstanding corrosive solutions by protecting the underlying material of an exposed surface. For example, certain biological assays require the use of corrosive solutions or other harsh conditions (e.g., high salt solutions, multiple solution washes, etc.), which can corrode material of the substrate or remove functional chemical moieties from the substrate surface. The inventors have recognized and appreciated that certain vapor phase reagents may be used to form exceptionally stable surface coatings on a substrate surface. Accordingly, in some aspects, the application provides methods of modifying a substrate surface which stabilize the substrate under harsh assay conditions and/or for an extended period of time.

In some aspects, the application relates to the discovery that a phosphorus-containing layer on a metallic or plastic surface enhances formation of a silane coating layer over the metallic or plastic surface. Previous techniques for surface modification have used liquid phosphonic acid derivatives to passivate metallic surfaces to functionalization by silanization, which was based on the prior assumption that the passivation layer blocks silanization to promote functionalization of a non-metallic surface. The inventors surprisingly found that a phosphorus-containing layer formed using a phosphonic acid derivative promotes silanization over metallic surfaces. Based on these discoveries, the inventors developed techniques which involve functionalizing a non-metallic surface prior to forming a phosphorus-containing layer on a metallic or plastic surface using a phosphonic acid derivative in vapor phase. In this way, the phosphorus-containing layer acts as a priming layer for downstream silanization to form a silane coating layer over the metallic or plastic surface.

In addition to the advantages described above, surface coatings can provide a more favorable interface for reagents in a biological assay, such as anti-fouling surface coatings which reduce or eliminate the adherence of reagent components in a biological reaction. Examples of surface coatings and surface modification processes which may be used in accordance with the application are described in U.S. Patent Publication No. US20180326412, entitled "SUBSTRATES HAVING MODIFIED SURFACE REACTIVITY AND ANTIFOULING PROPERTIES IN BIOLOGICAL REACTIONS," which is hereby incorporated by reference in its entirety.

Among other aspects, the application provides methods of forming a phosphorus-containing layer on a metallic or plastic surface. In some embodiments, a metallic surface may comprise metal, metal oxides (e.g., oxide anion, hydroxide), or a combination thereof. In some embodiments, a metallic surface comprises one or more transition metals. In some embodiments, a metal oxide surface is a transitional metal (i.e., transition metal) oxide surface. In some embodiments, a metal oxide surface may comprise titanium oxide (e.g., titanium dioxide), aluminum oxide, zirconium oxide, iron oxide, tin oxide, and/or tantalum oxide. In certain embodiments, the metallic surface is a titanium dioxide (TiO2) surface. In some embodiments, a plastic surface may comprise polyethylene, polypropylene, polystyrene, polycarbonate, polyvinyl chloride, polytetrafluoroethylene, or a combination thereof.

In some embodiments, a metallic or plastic surface may be pretreated or cleaned prior to or at the beginning of a surface modification process described herein. In some embodiments, the surface may be subjected to a plasma cleaning process at prior to or at the beginning of the surface modification process. For example, in some embodiments, the surface may be exposed to plasma, radicals, excited species, and/or atomic species. In some embodiments, the surface may be thermally treated with exposure to hydrogen, ammonia, and/or mixtures thereof. In some embodiments, the surface is treated with an oxygen plasma, tetrabutylammonium hydroxide, potassium hydroxide in methanol, hydrogen peroxide in sulfuric acid (e.g., a "piranha" solution), nitric acid in sulfuric acid, hydrogen peroxide in ammonia, sulfuric acid, hydrofluoric acid, EDTA, or a combination of these treatments prior to forming a phosphorus-containing layer on the surface. In some embodiments, a pretreated surface comprises exposed hydroxide and/or oxide anion functional groups.

As used herein, in some embodiments, a phosphorus-containing layer refers to an assembly of phosphorus-containing molecules adsorbed from a vapor phase precursor (e.g., a phosphoryl halide in vapor phase) on a surface. In some embodiments, a phosphorus-containing molecule of the layer comprises an organic tail and a terminal phosphorus-containing moiety, where the molecule is adsorbed on the surface through the phosphorus-containing moiety such that the organic tail is distal to the surface relative to the phosphorus-containing moiety. Examples of phosphorus-containing moieties include, without limitation, phosphonate or phosphonic acid, phosphonite, phosphate, phosphite, phosphonamidate, phosphoramidate, and other such organophosphorus functional groups known in the art. Accordingly, in some embodiments, a phosphorus-containing layer is an organic organophosphorus layer, such as an organophosphonate layer. In some embodiments, a phosphorus-containing layer is a self-assembled monolayer (SAM), which is a relatively ordered assembly of molecules that spontaneously adsorb on a metallic or plastic surface from a precursor reagent in vapor phase.

In accordance with the application, a phosphorus-containing layer (e.g., an organic layer) is formed on a metallic or plastic surface by treating the surface with a reagent in vapor phase (e.g., an organic reagent in vapor phase, such as a phosphoryl halide). In some aspects, the application provides methods of forming a stable surface coating on one or more surface portions of a substrate. In some embodiments, a stable surface coating refers to a surface coating that comprises a phosphorus-containing layer and a coating layer (e.g., a silane coating layer).

In some embodiments, a coating layer is formed over a metallic or plastic surface after a phosphorus-containing layer is formed on the metallic or plastic surface. In some embodiments, one portion of a coating layer is formed on the metallic or plastic surface and another portion of the coating layer is formed on the phosphorus-containing layer. In some embodiments, one portion of a coating layer is formed over a first surface portion of a substrate (e.g., over a metallic or plastic surface) and another portion of the coating layer is formed over a second surface portion of the substrate (e.g., over a transparent or glass surface). In some embodiments, a coating layer is formed by treating a surface with at least one silane in vapor phase. In some embodiments, the at least one silane is a chlorosilane, such as a chlorosiloxane, alkylchlorosilane, or a mixture thereof. In some embodiments, the at least one silane adsorbs on a metallic or plastic surface. In some embodiments, the at least one silane adsorbs on a phosphorus-containing layer. In some embodiments, the at least one silane adsorbs on a transparent or glass surface.

As used herein, a vapor phase reagent, or a reagent in vapor phase refers to a vapor-to-solid precursor that is, or comprises, a molecule that may undergo a vapor-to-solid deposition reaction. In some embodiments, a vapor refers to a gas, a vapor, and/or an aerosol. In some embodiments, a vapor refers to a gas-phase material (e.g., a gas or vapor) or a material otherwise dispersed in a volume that may be occupied by a gas, vapor, or aerosol (e.g., liquid droplets sprayed or injected into a volume). A vapor-to-solid deposition refers to a reaction in which a molecule or material in vapor phase forms one or more solid-state deposition products. For example, in some embodiments, a vapor-to-solid deposition reaction is a decomposition reaction. A vapor-to-solid decomposition reaction may result in at least one vapor state product and at least one solid state product. A vapor state product refers to a molecule whose physical state of matter is as a gas, vapor, or aerosol. A solid state product refers to an atom, ion, compound, molecule, or combination of these, whose physical state of matter is as a solid. The solid phase deposition product of a vapor-to-solid precursor may contribute to formation of a solid material such as a phosphorus-containing layer and/or a coating layer as described herein.

Accordingly, in some embodiments, formation of a phosphorus-containing layer and/or a coating layer can involve a chemical and/or physical transformation of the one or more reagents in vapor phase. For example, during treatment of a surface with a phosphoryl halide in vapor phase, the phosphoryl halide can decompose to a vapor phase product in the form of halide gas and a solid phase product in the form of a phosphoryl layer on the surface (e.g., a phosphorus-containing layer). In some embodiments, a phosphorus-containing layer forms through covalent attachment of the phosphoryl to the surface. By way of example, a phosphorus atom of the phosphoryl can be bound by hydroxide and/or oxide anion functional groups on the surface, such that the phosphoryl is covalently attached through a phosphonate group. In some embodiments, the phosphorus-containing layer forms on the surface without the formation of a covalent bond, being held in place, for example by van der Waals, hydrogen bonding, or dipolar forces.

In some embodiments, a vapor phase reagent of the application may be suitable for chemical vapor deposition (CVD), atomic layer deposition (ALD), molecular beam epitaxy (MBE), physical vapor deposition (PVD), or any combination of these deposition processes. A vapor phase reagent may be a CVD precursor and/or an ALD precursor. CVD and ALD are non-limiting examples of vapor-to-solid deposition processes for deposition of a solid material from a vapor phase precursor. Examples of CVD processes include, without limitation, metal-organic CVD (MOCVD), plasma-enhanced CVD (PECVD), microwave plasma-assisted CVD (MWCVD or MPCVD), hot filament CVD (HFCVD), photo-initiated CVD (PICVD), laser CVD (LCVD), vapor-phase epitaxy (VPE), and ALD. Deposition of the vapor phase reagent may involve reaction of the reagent with a substrate or a receiving surface thereof. In some embodiments, a substrate is exposed simultaneously and/or sequentially to a plurality of types of vapor phase reagents to deposit a solid material, such as a phosphorus-containing layer and/or a coating layer as described herein.

In some aspects, the application provides methods and compositions for modifying a surface. As used herein, in some embodiments, a surface refers to a surface of a substrate or solid support. In some embodiments, a substrate refers to a material, layer, or other structure having a surface, such as a receiving surface, that is capable of supporting a deposited material, such as a layer or a coating described herein. In some embodiments, a receiving surface of a substrate may optionally have one or more features, including nanoscale or microscale recessed features such as an array of sample wells. In some embodiments, an array is a planar arrangement of elements such as sensors or sample wells. An array may be one or two dimensional. A one dimensional array is an array having one column or row of elements in the first dimension and a plurality of columns or rows in the second dimension. The number of columns or rows in the first and second dimensions may or may not be the same. In some embodiments, the array may include, for example, $10^2$, $10^3$, $10^4$, $10^5$, $10^6$, or $10^7$ sample wells.

In certain embodiments, a sample well of the array comprises a top opening that extends into the substrate to a bottom surface distal to the top opening, and wherein the sample well comprises a side wall surface disposed between the top opening and the bottom surface. In certain embodiments, the side wall surface comprises the first surface portion; the bottom surface comprises the second surface portion; and the phosphoryl halide preferentially forms the phosphorus-containing layer on the side wall surface of the sample well.

In some aspects, the application provides methods of modifying one or more surfaces of a sample well. In some embodiments, a sample well comprises a confinement region which can be a physical or chemical attribute of a substrate that permits the localization of a molecule or reaction of interest. In some embodiments, a confinement region may be a discrete region of a surface of a substrate that binds a molecule of interest, such as a bottom surface of a sample well having a polypeptide or a nucleic acid coupled to such surface. In some embodiments, sample wells comprise hollows or wells having defined shapes and volumes which are manufactured into a substrate or device. Sample wells can be fabricated using techniques described in the art, for example, as disclosed in U.S. application Ser. No. 16/555,902, the content of which is incorporated herein by reference in its entirety.

FIG. 1A schematically illustrates an example of sample well surface functionalization in accordance with aspects of the application. A cross-sectional view of a sample well 100 is shown, the sample well having a metallic surface 102 and a silica surface 104. For illustrative purposes, sample well 100 is depicted as being defined by side walls extending from a top surface to a bottom surface, where metallic surface 102 is formed on the side walls and top surface, and silica surface 104 is formed on the bottom surface.

It should be appreciated that, in some embodiments, any of the features defining sample well 100 (side walls, top surface, bottom surface) may have different or additional surface properties. For example, in some embodiments, sample well 100 is defined by side walls extending into the material of the bottom surface, such that one portion of silica surface 104 is formed on the side walls and another portion of silica surface 104 is formed on the bottom surface. In this configuration, the side walls of sample well 100 would include silica surface 104 formed on a surface portion proximal to the bottom surface and metallic surface 102 formed on a surface portion distal to the bottom surface.

In process (I), sample well 100 is treated with a functionalizing agent 108 that preferentially binds silica surface 104 to form a functionalized surface 106. The functionalizing agent 108 comprises a coupling moiety which provides a coupling functionality to the bottom surface of sample well 100. As shown, in some embodiments, functionalized surface 106 comprises functionalizing agent 108 and a silane

110 that does not comprise the coupling moiety. Accordingly, in some embodiments, functionalized surface 106 is formed in process (I) by treating sample well 100 with a mixture comprising functionalizing agent 108 and silane 110. In some embodiments, functionalizing agent 108 is a biotinylated silane (e.g., biotin-PEG-silane) and silane 110 is a non-biotinylated silane (e.g., PEG-silane).

In some embodiments, a functionalizing agent as described herein comprises a coupling moiety. In some embodiments, the coupling moiety is a covalent coupling moiety. Examples of covalent coupling moieties include, without limitation, a trans-cyclooctene (TCO) moiety, a tetrazine moiety, an azide moiety, an alkyne moiety, an aldehyde moiety, an isocyanate moiety, an N-hydroxysuccinimide moiety, a thiol moiety, an alkene moiety, a dibenzocyclooctyl moiety, a bicyclononyne moiety, and a thiamine pyrophosphate moiety. Examples of functionalizing agents that comprise a covalent coupling moiety include, without limitation, azide-silanes and azide-organosilanes, such as azide-PEG-silane (e.g., azide-PEGS-silane, azide-PEGS-silane) and azide-alkylsilane (e.g., azide-C11-silane). In some embodiments, the coupling moiety is a non-covalent coupling moiety. Examples of non-covalent coupling moieties include, without limitation, a biotin moiety, an avidin protein, a streptavidin protein, a lectin protein, and a SNAP-tag. In certain embodiments, the functionalizing agent comprises a moiety capable of preferentially binding to silica.

In certain embodiments, the moiety capable of preferentially binding to silica is a silane. In certain embodiments, the silane is a mono-ethoxysilane, methoxysilane, di-ethoxysilane, trichlorosilane, or di-ethoxy-methoxysilane. In certain embodiments, the functionalizing agent comprises a biotinylated silane.

In some embodiments, functionalizing agent 108 and silane 110 can be provided in a ratio that is determined based on a desired density of coupling moiety on the surface to be functionalized. For example, in some embodiments, a functionalized surface is formed using a mixture comprising a functionalizing agent and a silane in a molar ratio of at least 5-fold excess silane over functionalizing agent. In some embodiments, the mixture comprises between about 5-fold excess and about 250-fold excess silane over functionalizing agent (e.g., between about 5-fold and about 100-fold, between about 5-fold and about 50-fold, between about 50-fold and about 250-fold, between about 100-fold and about 250-fold, or between about 50-fold and about 150-fold excess silane over functionalizing agent).

In process (II), sample well 100 is treated with a phosphoryl halide in vapor phase to form a phosphorus-containing layer 112. As shown, in some embodiments, the phosphoryl halide preferentially forms phosphorus-containing layer 112 on metallic surface 102. In some embodiments, the phosphoryl halide preferentially forms the phosphorus-containing layer on the metallic surface (e.g., a first surface portion of the sample well) with about 2-fold to about 60-fold selectivity. In some embodiments, the phosphoryl halide preferentially forms the phosphorus-containing layer on the metallic surface with about 4-fold to about 40-fold selectivity. In some embodiments, the phosphoryl halide preferentially forms the phosphorus-containing layer on the metallic surface with about 8-fold to about 20-fold selectivity.

In process (III), sample well 100 is treated with at least one silane to form a coating layer 114 over metallic surface 102 and silica surface 104. In some embodiments, coating layer 114 is formed by treating sample well 100 with a single composition that comprises one or more silanes (e.g., one type or a mixture of types of silanes). For example, in some embodiments, coating layer 114 is formed by co-deposition of more than one type of silane. In some embodiments, coating layer 114 is formed by backfill silanization as illustrated in FIG. 1B.

Figure 1B:
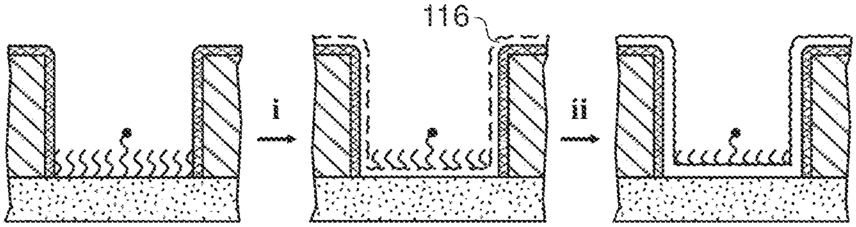

FIG. 1B schematically illustrates an example of forming coating layer 114 by backfill silanization. In process (i), sample well 100 is treated with a first silane to form a partial coating layer 116 over metallic surface 102 and silica surface 104. In process (ii), sample well 100 is treated with a second silane to form coating layer 114. In some embodiments, the first and second silanes are the same. In some embodiments, the first and second silanes are different (e.g., different types of silanes).

In some embodiments, a coating layer as described herein can be formed over a surface by deposition, co-deposition, or backfill silanization by treating the surface with one or more silanes in vapor phase. Silanes which can be used in vapor phase treatment include any silane compound with a favorable boiling point or flash point (e.g., below ~200° C.) at vacuum. Examples of silanes in vapor phase which may be used to form a coating layer include halogenated silanes (e.g., chlorosilanes, such as chlorosiloxanes, alkylchlorosilanes, alkyldichlorosilanes, alkyltrichlorosilanes), alkoxysilanes (e.g., mono-, di-, and trialkoxysilanes), silicon hydrides (e.g., hexylsilane), and aza-silanes including both linear and cyclic (e.g., hexamethyldisilazane), and thiasilanes including both linear and cyclic (e.g., 2,2,4-Trimethyl-1-thia-2-silacyclopentane). Specific examples of chlorosilanes include, without limitation, hexachlorodisiloxane, chloro(hexyl)dimethylsilane, hexyldichlorosilane, and hexyltrichlorosilane. Specific examples of alkoxysilanes include, without limitation, methoxytrimethylsilane, dimethoxydimethylsilane, and hexyltrimethoxysilane.

Figure 1C:
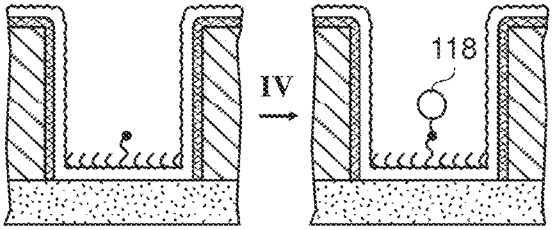

As generically depicted in FIGS. 1A-1B, in some embodiments, a portion of coating layer 114 is formed over silica surface 104 such that the coupling moiety of functionalizing agent 108 remains available for coupling a molecule of interest to functionalized surface 106. FIG. 1C illustrates an example whereby a molecule of interest is coupled to a functionalized surface of a substrate. In process (IV), sample well 100 is contacted with a molecule of interest 118 that binds to the coupling moiety of functionalizing agent 108. Examples of molecules of interest are described herein and include, without limitation, nucleic acids and polypeptides (e.g., proteins and protein fragments for use in a polypeptide sequencing reaction, and polymerizing enzymes, such as a nucleic acid polymerase for use in a nucleic acid sequencing reaction).

Figure 2:
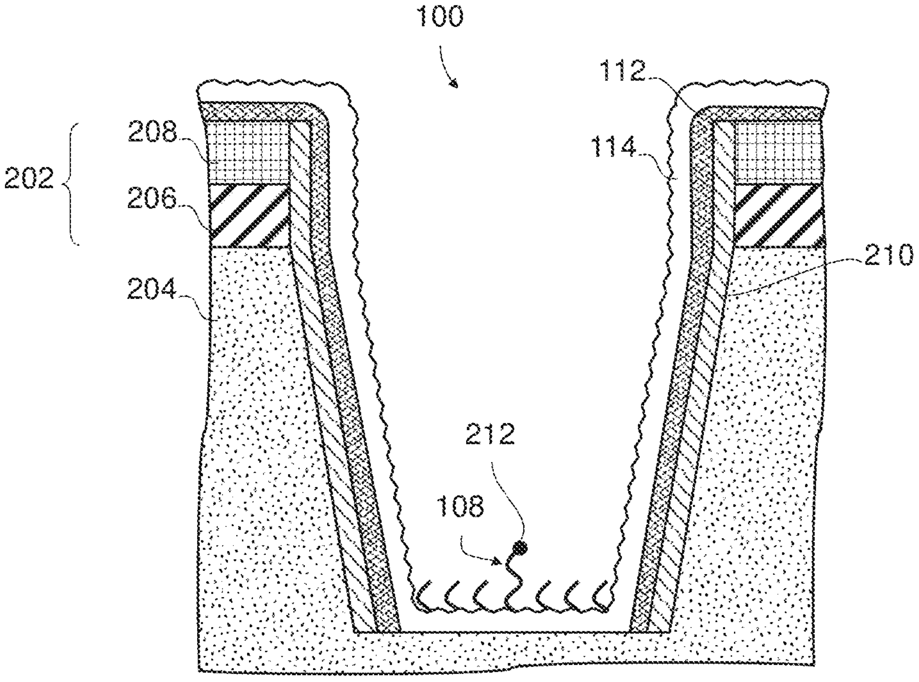
FIG. 2 shows an example of a sample well having modified surfaces in accordance with the application.

FIG. 2 is a cross-sectional view illustrating an example of a sample well 100 with surface modifications in accordance with the application. As shown in FIG. 2, the sample well 100 is defined by an opening formed through a metal stack 202 disposed on a cladding layer 204 (e.g., $SiO_2$). In some embodiments, sample well 100 is one of a plurality of sample wells formed on the surface of a device (e.g., a device comprising an array of sample wells). Metal stack 202 may include one or more layers of metal material(s) (e.g., aluminum, titanium, copper). As shown in FIG. 2, some embodiments of metal stack 202 include an aluminum layer 206 positioned proximate to the top of the cladding layer 204 and a titanium nitride layer 208 over the aluminum layer 206.

The aluminum layer 206 may include copper and/or silicon. In some embodiments, the aluminum layer 206 may include less than approximately 2% of copper and/or silicon, and may have a thickness in the range of about 30 nm to 150 nm, or any value or range of values within that range. In some embodiments, the aluminum layer is about 65 nm. The titanium nitride layer 208 may include a layer of titanium in contact with the aluminum layer 206 and have a thickness of in the range of 1 nm to 150 nm, or any value or range of values within that range. In some embodiments, the thickness of titanium nitride layer 208 is approximately 80 nm.

In order to facilitate selective chemical functionalization for coupling a molecule of interest at the bottom of the sample well 100, the bottom surface of the sample well 100 should have a different composition than other surfaces (e.g., the side walls of the sample well 100). As shown in FIG. 2, the bottom surface of the sample well may be the material of the cladding layer (e.g., exposed $SiO_2$), and the side walls of the sample well 100 may be a spacer material 210. Spacer material 210 may include one or more metal oxides (e.g., $TiO_2$, $Al_2O_3$, $SiO_2$, TiN, $HfO_2$, $ZrO_2$, and $Ta_2O_5$). The top surface of the array may include one or more metal oxide materials formed by oxidation of the top surface of layer 208 (e.g., $TiO_2$ formed by oxidation of TiN).

In some embodiments, it may be desired to have the exposed surfaces of the array (top surface of layer 208, sample well side walls, bottom surface) be substantially stable for particular types of solutions, including those used during surface modification and during an assay. For example, certain conditions that are used for an assay may include corrosive solutions or otherwise harsh treatment conditions (e.g., high ionic strength aqueous solutions, cycling of multiple solutions, high or low pH solutions, etc.). In accordance with the application, surface modification processes may be used to produce an array with one or more layers and/or coatings on the exposed surfaces which may be substantially stable when in contact with such solutions for a desired period of time.

As shown in FIG. 2, a sample well 100 produced in accordance with the surface modification techniques of the application can include a functionalizing agent 108 that comprises a coupling moiety 212 on the exposed surface of the cladding layer 204 which defines the bottom surface of the sample well 100. Sample well 100 includes a phosphorus-containing layer 112 formed on the top surface of layer 208 and spacer material 210 (e.g., the metallic surface of sample well 100). As described herein, phosphorus-containing layer 112 may be formed by treating sample well 100 with a phosphoryl halide in vapor phase which preferentially forms phosphorus-containing layer 112 on the metallic surface of sample well 100. As shown, sample well 100 includes a coating layer 114 formed over the exposed surface of the cladding layer 204 (e.g., the silica surface) and over the top surface of layer 208 and spacer material 210 (e.g., the metallic surface). In some embodiments, coating layer 114 is a silane coating layer. In some embodiments, a stable surface coating of the application comprises phosphorus-containing layer 112 and coating layer 114.

Phosphoryl Halides

Methods described herein use phosphoryl halides as vapor phase reagents. A "phosphoryl halide" is an organic or inorganic compound comprising the group $>P(=O)(X^1)$, wherein $X^1$ is halogen. The phosphoryl halide can be a phosphoryl mono-, di-, or tri-halide, as described below. In certain embodiments, the phosphoryl halide is an organic phosphoryl halide. The term "organic" means that the reagent comprises one or more carbon atoms (i.e., at least one carbon-containing group). In certain embodiments, the phosphoryl halide is an organic phosphoryl halide and the phosphorus-containing layer is an organophosphorus layer.

The phosphoryl halide should have a molecular weight conducive for use in the vapor phase. In certain embodiments, the phosphoryl halide has a molecular weight of less than 500, 450, 400, 350, 300, 250, 200, or 150 g/mol. In certain embodiments, the phosphoryl halide has a molecular weight from about 132 g/mol to 260 g/mol, inclusive. In certain embodiments, the phosphoryl halide has a molecular weight from about 132 g/mol to 232 g/mol, inclusive. In certain embodiments, the phosphoryl halide has a molecular weight from about 203 g/mol to 232 g/mol, inclusive.

Phosphoryl Dihalides

In certain embodiments, the phosphoryl halide is a phosphoryl dihalide (i.e., comprising the group $-P(=O)(X^1)_2$, wherein each instance of $X^1$ is independently halogen). In certain embodiments, the phosphoryl dihalide is a phosphoryl dichloride. In certain embodiments, the phosphoryl dihalide is an organic phosphoryl dihalide. In certain embodiments, the phosphoryl dihalide is an organic phosphoryl dichloride.

In certain embodiments, the phosphoryl dihalide is an organic phosphonic dihalide (wherein $-P(=O)(X^1)_2$ is attached to a carbon). In certain embodiments, the phosphoryl dihalide is an organic phosphonic dichloride.

For example, in certain embodiments, the phosphoryl dihalide is of Formula (I):

(I)

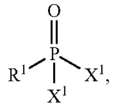

or a salt thereof, wherein:

each instance of $X^1$ is independently a halogen;

$R^1$ is optionally substituted alkyl, optionally substituted heteroalkyl, optionally substituted alkenyl, optionally substituted alkynyl, optionally substituted carbocyclyl, optionally substituted heterocyclyl, optionally substituted aryl, or optionally substituted heteroaryl, $-OR^O$, or $-N(R^N)_2$;

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group; or optionally two $R^O$ are taken together with the intervening atoms to form optionally substituted heterocyclyl;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are taken together with the intervening atoms to form optionally substituted heterocyclyl.

As described herein, each instance of $X^1$ is independently halogen. In certain embodiments, each instance of $X^1$ is independently —Cl or —Br. In certain embodiments, each instance of $X^1$ is —Cl. In certain embodiments, each instance of $X^1$ is —Br.

In certain embodiments, the compound of Formula (I) is of the formula:

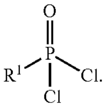

In certain embodiments, $R^1$ is optionally substituted alkyl. In certain embodiments, $R^1$ is optionally substituted $C_{1-10}$ alkyl. In certain embodiments, $R^1$ is optionally substituted $C_{1-8}$ alkyl. In certain embodiments, $R^1$ is unsubstituted $C_{1-8}$ alkyl. In certain embodiments, $R^1$ is optionally substituted $C_{6-8}$ alkyl. In certain embodiments, $R^1$ is unsubstituted $C_{6-8}$ alkyl. In certain embodiments, $R^1$ is optionally substituted $C_6$ alkyl. In certain embodiments, $R^1$ is unsubstituted $C_6$ alkyl. In certain embodiments, $R^1$ is optionally substituted $C_8$ alkyl. In certain embodiments, $R^1$ is unsubstituted $C_8$ alkyl.

In certain embodiments, $R^1$ is selected from the group consisting of methyl, ethyl, n-propyl, iso-propyl, n-butyl, iso-butyl, sec-butyl, or tert-butyl.

In certain embodiments, $R^1$ is selected from the group consisting of:

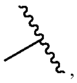, 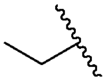, 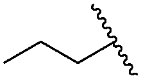, 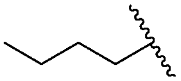, 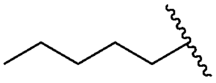, 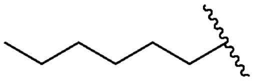, 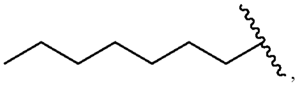, 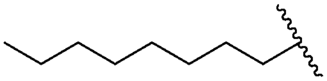, 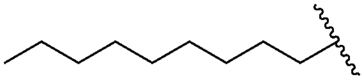, and 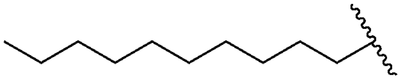.

For example, in certain embodiments, the phosphoryl halide (e.g., compound of Formula (I)) is a compound of one of the following formulae:

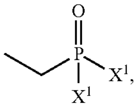, 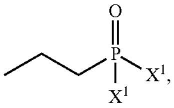, 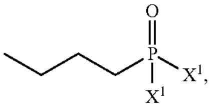, 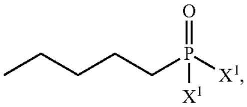, 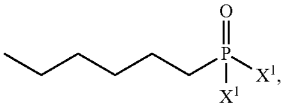, 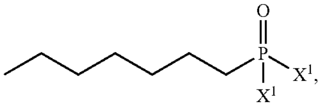, and

-continued

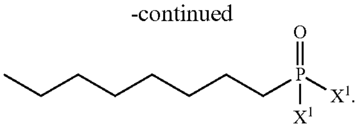.

For example, in certain embodiments, the phosphoryl halide is selected from the group consisting of:

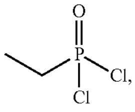, 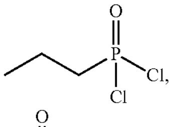, 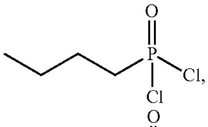, 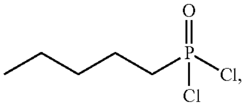, 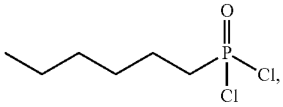, 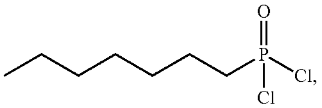, and 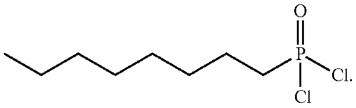.

In certain embodiments, $R^1$ is —$OR^O$. In certain embodiments, In certain embodiments, $R^1$ is —$OR^O$; and $R^O$ is optionally substituted aryl. In certain embodiments, $R^1$ is —$OR^O$; and $R^O$ is optionally substituted phenyl. In certain embodiments, $R^1$ is —$OR^O$; and $R^O$ is unsubstituted phenyl. In certain embodiments, $R^1$ is —$OR^O$; and $R^O$ is phenyl substituted with halogen or —$NO_2$.

For example, in certain embodiments, the phosphoryl halide is selected from the group consisting of:

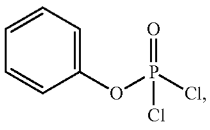, 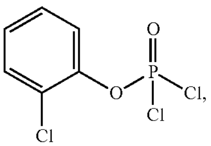, 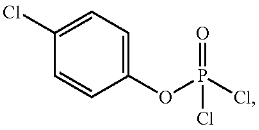, 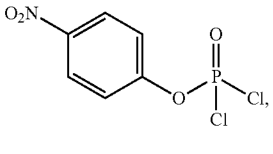, and 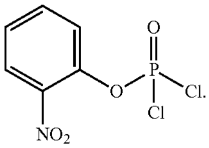.

Other examples of phosphoryl halides (i.e., compounds of Formula (I)) include, but are not limited to, the following:

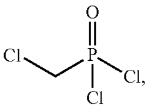, 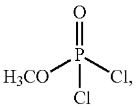, 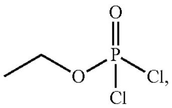, and

-continued

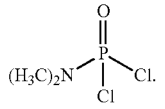

In certain embodiments, $R^1$ is a polymeric group (e.g., polyethylene glycol (PEG)). In certain embodiments, $R^1$ is a polyfluoroalkyl group.

In certain embodiment, the phosphoryl halide (i.e., compound of Formula (I)) is of Formula (I-a):

(I-a)

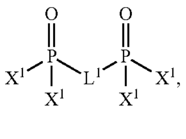

or a salt thereof, wherein:

$L^1$ is optionally substituted alkylene.

In certain embodiments, the compound of Formula (I-a) is of the formula:

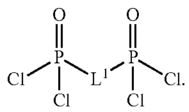

In certain embodiments, $L^1$ is optionally substituted $C_{1-6}$ alkylene. In certain embodiments, $L^1$ is unsubstituted $C_{1-6}$ alkylene. In certain embodiments, $L^1$ is of one of the following formulae:

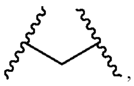, 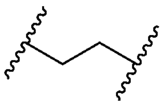, 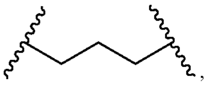, 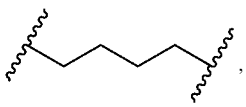, 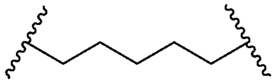, or 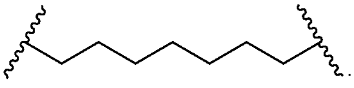.

For example, in certain embodiments, the phosphoryl halide (i.e., compound of Formula (I-a)) is the following:

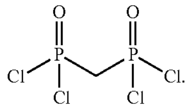

Phosphoryl Monohalides

In certain embodiments, the phosphoryl halide is a phosphoryl monohalide (i.e., comprising the group >P(=O)($X^1$), wherein $X^1$ is halogen. In certain embodiments, the phosphoryl monohalide is a phosphoryl monochloride. In certain embodiments, the phosphoryl monohalide is an organic phosphoryl monohalide. In certain embodiments, the phosphoryl monohalide is an organic phosphoryl monochloride.

In certain embodiments, the phosphoryl monohalide is an organic phosphinic dihalide (wherein >P(=O)$(X^1)_2$ is attached to two different carbon groups). In certain embodiments, the phosphoryl monohalide is an organic phosphinic chloride.

In certain embodiments, the phosphoryl halide is of Formula (II):

(II)

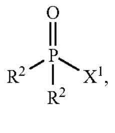

or a salt thereof, wherein:

$X^1$ is halogen;

each instance of $R^2$ is optionally substituted alkyl, optionally substituted heteroalkyl, optionally substituted alkenyl, optionally substituted alkynyl, optionally substituted carbocyclyl, optionally substituted heterocyclyl, optionally substituted aryl, or optionally substituted heteroaryl, —$OR^O$, or —$N(R^N)_2$;

or optionally two $R^2$ groups are taken together with the intervening atoms to form optionally substituted heterocyclyl.

each instance of $R^O$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or an oxygen protecting group; or optionally two $R^O$ are taken together with the intervening atoms to form optionally substituted heterocyclyl;

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, or a nitrogen protecting group; or optionally two $R^N$ are taken together with the intervening atoms to form optionally substituted heterocyclyl.

In certain embodiments, $X^1$ is —Cl or —Br. In certain embodiments, X is —Cl. In certain embodiments, the phosphoryl halide is of the formula:

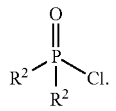

In certain embodiments, each instance of $R^2$ is independently optionally substituted alkyl. In certain embodiments, each instance of $R^2$ is independently optionally substituted $C_{1-10}$ alkyl. In certain embodiments, each instance of $R^2$ is independently optionally substituted $C_{1-6}$ alkyl. In certain embodiments, each instance of $R^2$ is independently unsubstituted $C_{1-6}$ alkyl.

In certain embodiments, each instance of $R^2$ is independently selected from the group consisting of methyl, ethyl, n-propyl, iso-propyl, n-butyl, iso-butyl, sec-butyl, or tert-butyl.

In certain embodiments, each instance of $R^2$ is independently selected from the group consisting of:

, 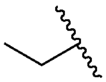, 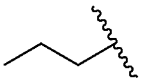, 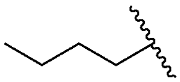, 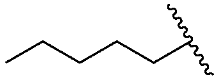, 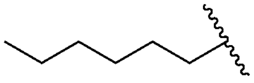, 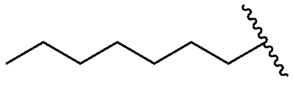, 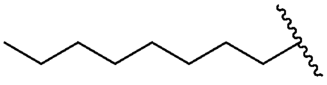, 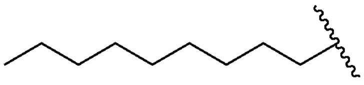, and 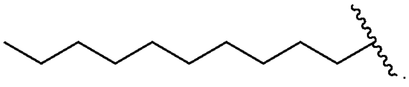.

For example, in certain embodiments, the phosphoryl halide (i.e., compound of Formula (II)) is the following:

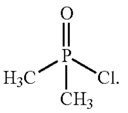

In certain embodiments, each instance of $R^2$ is independently —$OR^O$; and each instance of $R^O$ is independently optionally substituted alkyl. In certain embodiments, each instance of $R^2$ is independently —$OR^O$; and each instance of $R^O$ is independently optionally substituted $C_{1-10}$ alkyl. In certain embodiments, each instance of $R^2$ is independently —$OR^O$; and each instance of $R^O$ is independently optionally substituted $C_{1-6}$ alkyl. In certain embodiments, each instance of $R^2$ is independently —$OR^O$; and each instance of $R^O$ is independently unsubstituted $C_{1-6}$ alkyl.

For example, in certain embodiments, the phosphoryl halide (i.e., compound of Formula (II)) is one of the following:

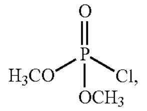 and 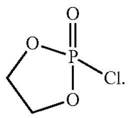

Phosphoryl Trihalides

In certain embodiments, the phosphoryl halide is a phosphoryl trihalide (i.e., of the formula $P(=O)(X^1)_3$, wherein each instance of $X^1$ is independently halogen). In certain embodiments, the phosphoryl halide is phosphoryl trichloride. In certain embodiments, the phosphoryl halide is phosphoryl tribromide.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_1$-6, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

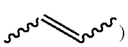)

may be an (E)- or (Z)-double bond.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

The term "unsaturated bond" refers to a double or triple bond. The term "unsaturated" or "partially unsaturated" refers to a moiety that includes at least one double or triple bond. The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_3$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(=O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3{}^+X^-$, —$P(OR^{cc})_3{}^+X^-$, —$P(R^{cc})_4$, —$P(OR^{cc})_4$, —$OP(R^{cc})_2$, —$OP(R^{cc})_3{}^+X^-$, —$OP(OR^{cc})_2$, —$OP(OR^{cc})_3{}^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion; or two geminal hydrogens on a carbon atom are replaced with the group =O, =S, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$; each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(=O)R^{aa}$, $—C(=O)N(R^{cc})_2$, $—CO_2R^{aa}$, $—SO_2R^{aa}$, $—C(=NR^{cc})OR^{aa}$, $—C(=NR^{cc})N(R^{cc})_2$, $—SO_2N(R^{cc})_2$, $—SO_2R^{cc}$, $—SO_2OR^{cc}$, $—SOR^{aa}$, $—C(=S)N(R^{cc})_2$, $—C(=O)SR^{cc}$, $—C(=S)SR^{cc}$, $—P(=O)(R^{aa})_2$, $—P(=O)(OR^{cc})_2$, $—P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_3$-10 carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; each instance of $R^{dd}$ is, independently, selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3^+X^-$, $—N(OR^{ee})R^{ff}$, —SH, $—SR^{ee}$, $—SSR^{ee}$, $—C(=O)R^{ee}$, $—CO_2H$, $—CO_2R^{ee}$, $—OC(=O)R^{ee}$, $—OCO_2R^{ee}$, $—C(=O)N(R^{ff})_2$, $—OC(=O)N(R^{ff})_2$, $—NR^{ff}C(=O)R^{ee}$, $—NR^{ff}CO_2R^{ee}$, $—NR^{ff}C(=O)N(R^{ff})_2$, $—C(=NR^{ff})OR^{ee}$, $—OC(=NR^{ff})R^{ee}$, $—OC(=NR^{ff})OR^{ee}$, $—C(=NR^{ff})N(R^{ff})_2$, $—OC(=NR^{ff})N(R^{ff})_2$, $—NR^{ff}C(=NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(=O)R^{ee}$, $—Si(R^{ee})_3$, $—OSi(R^{ee})_3$, $—C(=S)N(R^{ff})_2$, $—C(=O)SR^{ee}$, $—C(=S)SR^{ee}$, $—SC(=S)SR^{ee}$, $—P(=O)(OR^{ee})_2$, $—P(=O)(R^{ee})_2$, $—OP(=O)(R^{ee})_2$, $—OP(=O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion; each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, $—NO_2$, $—N_3$, $—SO_2H$, $—SO_3H$, —OH, $—OC_{1-6}$ alkyl, $—ON(C_{1-6}\text{ alkyl})_2$, $—N(C_{1-6}\text{ alkyl})_2$, $—N(C_{1-6}\text{ alkyl})_3^+X^-$, $—NH(C_{1-6}\text{ alkyl})_2^+X^-$, $—NH_2(C_{1-6}\text{ alkyl})^+X^-$, $—NH_3^+X^-$, $—N(OC_{1-6}\text{ alkyl})(C_{1-6}\text{ alkyl})$, $—N(OH)(C_{1-6}\text{ alkyl})$, —NH(OH), —SH, $—SC_{1-6}$ alkyl, $—SS(C_{1-6}\text{ alkyl})$, $—C(=O)(C_{1-6}\text{ alkyl})$, $—CO_2H$, $—CO_2(C_{1-6}\text{ alkyl})$, $—OC(=O)(C_{1-6}\text{ alkyl})$, $—OCO_2(C_{1-6}\text{ alkyl})$, $—C(=O)NH_2$, $—C(=O)N(C_{1-6}\text{ alkyl})_2$, $—OC(=O)NH(C_{1-6}\text{ alkyl})$, $—NHC(=O)(C_{1-6}\text{ alkyl})$, $—N(C_{1-6}\text{ alkyl})C(=O)(C_{1-6}\text{ alkyl})$, $—NHCO_2(C_{1-6}\text{ alkyl})$, $—NHC(=O)N(C_{1-6}\text{ alkyl})_2$, $—NHC(=O)NH(C_{1-6}\text{ alkyl})$, $—NHC(=O)NH_2$, $—C(=NH)O(C_{1-6}\text{ alkyl})$, $—OC(=NH)(C_{1-6}\text{ alkyl})$, $—OC(=NH)OC_{1-6}$ alkyl, $—C(=NH)N(C_{1-6}\text{ alkyl})_2$, $—C(=NH)NH(C_{1-6}\text{ alkyl})$, $—C(=NH)NH_2$, $—OC(=NH)N(C_{1-6}\text{ alkyl})_2$, $—OC(=NH)NH(C_{1-6}\text{ alkyl})$, $—OC(=NH)NH_2$, $—NHC(=NH)N(C_{1-6}\text{ alkyl})_2$, $—NHC(=NH)NH_2$, $—NHSO_2(C_{1-6}\text{ alkyl})$, $—SO_2N(C_{1-6}\text{ alkyl})_2$, $—SO_2NH(C_{1-6}\text{ alkyl})$, $—SO_2NH_2$, $—SO_2(C_{1-6}\text{ alkyl})$, $—SO_2O(C_{1-6}\text{ alkyl})$, $—OSO_2(C_{1-6}\text{ alkyl})$, $—SO(C_{1-6}\text{ alkyl})$, $—Si(C_{1-6}\text{ alkyl})_3$, $—OSi(C_{1-6}\text{ alkyl})_3$-$C(=S)N(C_{1-6}\text{ alkyl})_2$, $C(=S)NH(C_{1-6}\text{ alkyl})$, $C(=S)NH_2$, $—C(=O)S(C_{1-6}\text{ alkyl})$, $—C(=S)SC_{1-6}$ alkyl, $—SC(=S)SC_{1-6}$ alkyl, $—P(=O)(OC_{1-6}\text{ alkyl})_2$, $—P(=O)(C_{1-6}\text{ alkyl})_2$, $—OP(=O)(C_{1-6}\text{ alkyl})_2$, $—OP(=O)(OC_{1-6}\text{ alkyl})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$ alkynyl, $C_3$-10 carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "acyl" refers to a group having the general formula $—C(=O)R^{X1}$, $—C(=O)OR^{X1}$, $—C(=O)—O—C(=O)R^{X1}$, $—C(=O)SR^{X1}$, $—C(=O)N(R^{X1})_2$, $—C(=S)R^{X1}$, $—C(=S)N(R^{X1})_2$, $—C(=S)O(R^{X1})$, $—C(=S)S(R^{X1})$, $—C(=NR^{X1})R^{X}$, $—C(=NR^{X1})OR^{1}$, $—C(=NR^{X1})SR^{X1}$, and $—C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di aliphaticamino, mono- or diheteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{bb})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(OR^{cc})_2$, —$P(=O)(R^{aa})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The invention is not intended to be limited in any manner by the above exemplary listing of substituents.

Other Definitions

As used herein, a "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

EXAMPLES

These and other aspects of the present invention will be further appreciated upon consideration of the following Examples, which are intended to illustrate certain particular embodiments of the invention but are not intended to limit its scope, as defined by the claims.

Example 1. Vapor Phase Phosphonic Dichloride for Surface Modification

Selectivity of vapor phase phosphonic dichloride for surface modification was evaluated by contact angle measurement and X-ray photoelectron spectroscopy (XPS). A coupon having surface regions composed of $TiO_2$ and $SiO_2$ was treated with vapor phase octylphosphonic dichloride (PDC) by chemical vapor deposition, which was expected to form a surface coating with hydrophobic characteristics.

Figure 3:
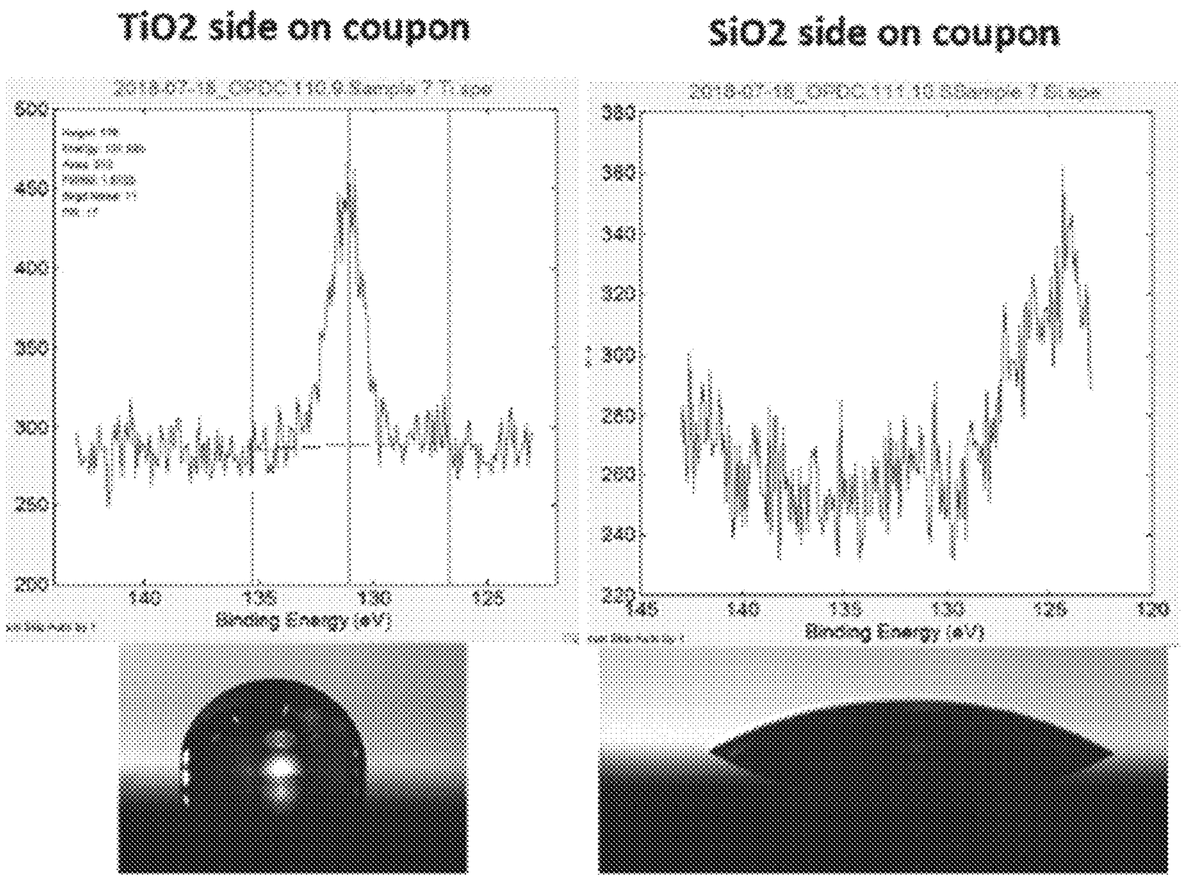
FIG. 3 shows spectra obtained from X-ray photoelectron spectroscopy (XPS) and imaging from wettability measurements, which collectively demonstrated high selectivity of vapor phase phosphonic dichloride for metal oxide surface.

Example results from selectivity experiments are shown in FIG. 3. The $TiO_2$ side of the surface-modified coupon produced a high contact angle (~99°) from wettability measurements (FIG. 3, left image) and showed a high phosphorus signal based on XPS measurements (FIG. 3, left spectrum). The $SiO_2$ side produced a relatively lower contact angle (~30°) from wettability measurements (FIG. 3, right image) and showed an undetectable phosphorus signal based on XPS measurements (FIG. 3, right spectrum). These results show that vapor deposition of PDC forms a coating on metal oxide surfaces relative to silica surfaces with high selectivity.

Figure 4A:
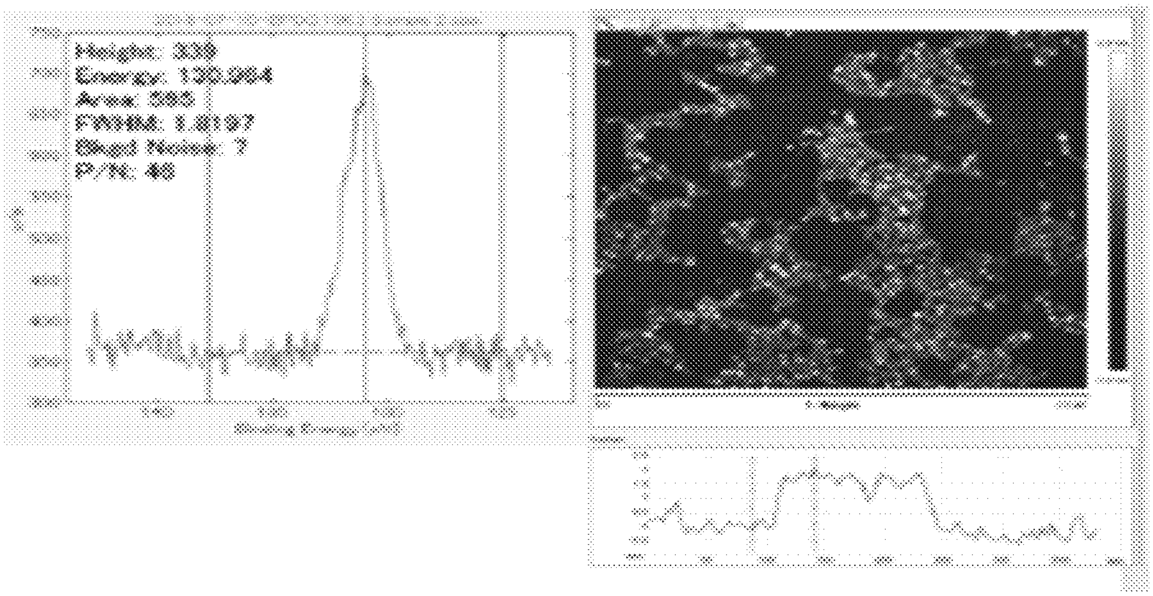
FIGS. 4A-4B show spectra obtained from XPS and imaging from atomic force microscopy (AFM).
Figure 4B:
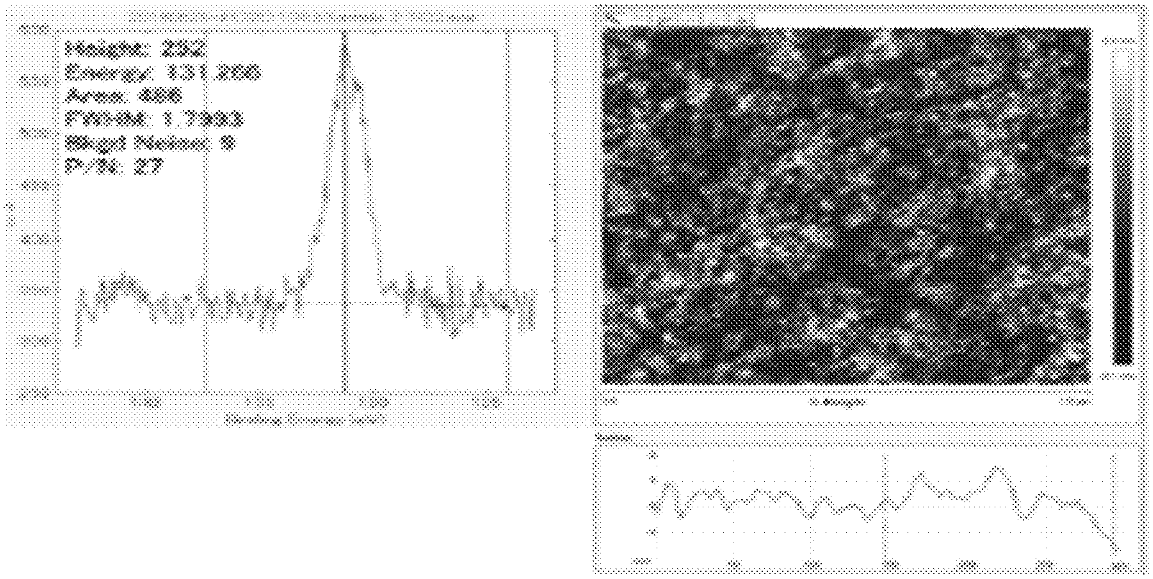

Surface coverage of coatings formed using liquid phase hexylphosphonic acid (HPA) or vapor phase PDC were compared. Based on data from XPS and atomic force microscopy (AFM), vapor phase PDC coating achieved better coverage in a more uniform format as compared to liquid phase coating (FIGS. 4A-4B). The HPA coated surface showed clear patches with height of about 2.7 nm which is the approximate size of 2-3 HPA molecules stacked end-to-end (FIG. 4A). By comparison, XPS and AFM data for the vapor phase PDC coating were consistent with formation of a uniform monolayer with more even surface distribution and coverage (FIG. 4B).

Example 2. Stable Silane Surface Coating for Corrosive Reaction Conditions

Corrosive reaction conditions during a biological reaction (e.g., sequencing) can potentially cause corrosion of an aperture structure on an array and cleavage of functional moiety on a functionalized bottom surface. To provide a stable coating layer capable of tolerating such conditions, a sample well having a functionalized silica surface and metal oxide side walls was silanized using hexachlorodisiloxane (HCDS) and a silane crosslinking coating.

Figures 5, 6:
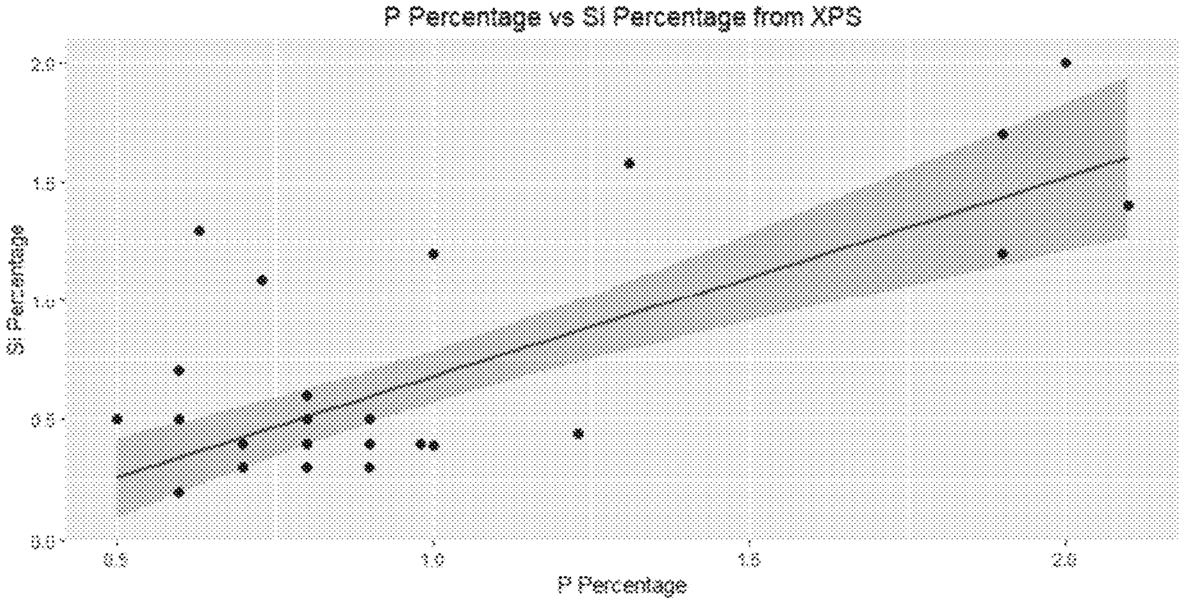
FIG. 5 shows data obtained by XPS for stability testing of silane surface coating.
FIG. 6 shows a plot of silicon percentage against phosphorus percentage of surface coatings as measured by XPS.

HCDS was used to introduce a relatively thick silane surface coating without blocking the access of a functional moiety (a terminal azide functional group) at the bottom surface. Process time was optimized to ensure the functional moiety was accessible for binding or reaction, and stability was evaluated by XPS of the silanized substrate after soaking in strong acid over 24 hours relative to an untreated control. The results indicated that the harsh chemical conditions are well tolerated by the HCDS coating (FIG. 5). Different silane crosslinking coatings (aminopropyltrimethoxysilane or hexyltrichlorosilane) were applied to the HCDS coating and both showed high durability and performance in biological sequencing reactions.

Example 3. Effects of Prior Organophosphorus Surface Coating on Silanization Sample well arrays having metal oxide surface portions and silica surface portions can be used to monitor biological reactions by immobilizing a molecule of interest to a functionalized silica surface of individual sample wells. Prior surface modification processes for preparing the functionalized silica surface involved first passivating metal oxide surfaces with an organophosphorus coating before functionalizing silica surfaces by silanization. Such processes were carried out on the assumption that the organophosphorus coating blocks silanization of metal oxide surfaces to promote selective functionalization of the silica surface.

After accumulating data from XPS on coating compositions of metal oxide surfaces over multiple array process batches, a clear positive proportional correlation was observed between phosphorus ("P Percentage") from organophosphorus coating and silicon ("Si Percentage") from downstream biotinylation silanization coating (FIG. 6). This observation indicated that an increasing amount of organophosphorus coating was promoting silanization of the metal oxide surface, which was inconsistent with the assumption that the organophosphorus coating blocks silanization.

To further evaluate the possibility that the organophosphorus coating was promoting downstream silanization, sample well arrays with and without organophosphorus coating (formed by vapor phase PDC) were treated with trialkoxy silane in vapor phase, and the silanized metal oxide surfaces were analyzed by XPS. The results for duplicate experiments are shown in Table 1.

TABLE 1

XPS results showing effect of prior PDC treatment on silanization

| Description | P Percentage (%) | Si Percentage (%) |
|---|---|---|
| Without prior PDC | 0.1 | 1.0 |
| Without prior PDC | 0.2 | 0.9 |
| With prior PDC | 1.4 | 1.6 |
| With prior PDC | 1.6 | 1.7 |

The XPS results in Table 1 show that the amount of silane on the organophosphorus coated metal oxide surface was approximately 60-70% higher than the amount of silane on metal oxide surfaces without organophosphorus coating. This data confirmed the initial observations which indicated that the organophosphorus coating promotes downstream silanization of metal oxide surface.

Figure 7:
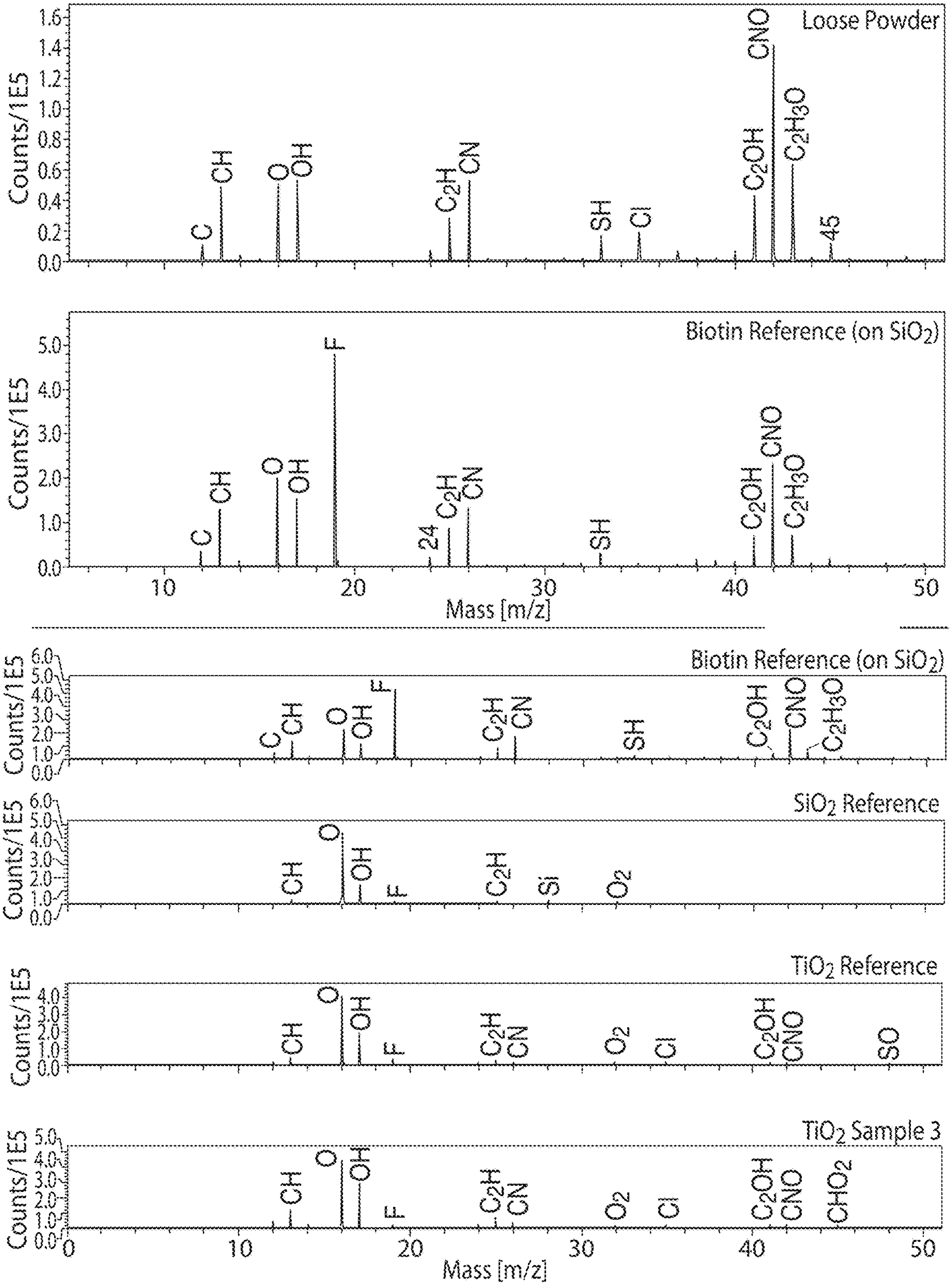
FIG. 7 shows spectra obtained by Time-of-Flight Secondary Ion Mass Spectrometry (TOF-SIMS) for control experiments used to determine characteristic fragment peaks of biotinylated silane.

The effects of prior organophosphorus coating on surface selectivity of functionalization by biotin-silane were quantitatively characterized by Time-of-Flight Secondary Ion Mass Spectrometry (TOF-SIMS). Control experiments were first carried out to determine characteristic fragment peaks of biotin-silane for both silica ($SiO_2$) and metal oxide ($TiO_2$) surfaces. Based on the spectra obtained during the control experiments (FIG. 7), the unique fragment peaks of biotin for both $TiO_2$ and $SiO_2$ surfaces were identified as: $CN^-$, $CNO^-$, $C_2H_5O^+$.

Substrates having $SiO_2$ surface and $TiO_2$ surface with or without organophosphorus coating were each treated with biotin-PEG-silane, and the biotinylated silanized substrate was subjected to TOF-SIMS. The relative amounts of fragment peaks were quantified, and these results are shown in FIG. 8. The fragment peak from $PO_2^-$ is shown to highlight that replicated "Sample 1" and "Sample 2" were coated by vapor phase PDC before biotinylation silanization, whereas replicated "Sample 3" and "Sample 4" were not coated by vapor phase PDC.

The data shown in FIG. 8 was further analyzed to quantify the selectivity of biotinylation silanization for the $SiO_2$ surface relative to the $TiO_2$ surface of the substrates tested. FIG. 9 shows the results of this analysis for the unique fragment peaks of biotin ($C_2H_5O^+$, $CNO^-$, $CN^-$). Selectivity ($SiO_2/TiO_2$) was calculated for each fragment peak using the formula shown in the panel at the top of FIG. 9.

The calculated biotinylation selectivity of $SiO_2/TiO_2$ from fragmented ions in both positive and negative mode consistently demonstrated that substrates without organophosphorus coating on $TiO_2$ (Samples 3 and 4) showed higher selectivity for biotinylation silanization of $SiO_2$ surface than the substrates with organophosphorus coating on $TiO_2$ (Samples 1 and 2). Based on the experimental observations and data, it was determined that prior organophosphorus coating of a metal oxide surface promotes formation of a silanization coating over the metal oxide surface rather than blocking silanization as previously thought.

Example 4. Scalable Surface Modification in Vapor Phase

After determining that organophosphorus coatings promote silanization of metal oxide surfaces, a surface modification process for a sample well array was devised in which biotinylation silanization of $SiO_2$ surface was carried out before vapor phase PDC coating of $TiO_2$ surface. The array was then treated with silanes to form an overlay over both surface compositions based on the theory that the organophosphorus coating formed on $TiO_2$ surface by PDC acts as a priming layer to promote silanization. Chemical and physical characterization of the processed array indicated hydrophobic behavior of the silanized surface, with a contact angle of around 90°, complete coverage of coating on chip with scale-like morphology in AFM images, and high percentage of representative elements (Si and P) detected in XPS spectrum (FIG. 10).

The total process time was approximately 5 hours, including initial plasma activation and intermittent steps of rinsing and drying. After activation and rinsing/drying, the array was treated for approximately 1 hour with a liquid phase mixture of PEG-silane and biotin-PEG-silane for bottom surface functionalization. After rinsing and drying, the array was treated with vapor phase octylphosphonic dichloride by chemical vapor deposition for approximately 30 minutes for side wall surface priming. The array surfaces were then treated with HCDS and hexyltrichlorosilane by chemical vapor deposition for approximately 2.5 hours to form the stable silane coating layer over sample well surfaces.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of modifying a surface of a substrate, the method comprising:

a) providing a substrate having a first surface portion and a second surface portion, wherein the substrate comprises a phosphorus-containing layer on the first surface portion, and wherein the first and second surface portions have different surface properties;

b) treating the substrate with a first silane composition in liquid phase, wherein the first silane composition comprises a silane functionalizing agent that comprises a coupling moiety, and wherein the silane functionalizing agent preferentially functionalizes the second surface portion; and c) following (a) and (b), treating the substrate with a second silane composition in vapor phase, wherein the second silane composition forms a silane coating layer over the first and second surface portions.

2. The method of claim 1, wherein the first surface portion is a metal or metal oxide surface, and wherein the second surface portion is a transparent or glass surface.

3. The method of claim 2, wherein the first surface portion is a titanium dioxide surface, and wherein the second surface portion is a silicon dioxide surface.

4. The method of claim 1, wherein the coupling moiety is a covalent coupling moiety or a non-covalent coupling moiety.

5. The method of claim 4, wherein the non-covalent coupling moiety comprises a biotin moiety, an avidin protein, a streptavidin protein, a lectin protein, or a SNAP-tag.

6. The method of claim 1, wherein the silane functionalizing agent comprises a biotin-PEG-silane.

7. The method of claim 1, wherein the silane functionalizing agent comprises a mono-ethoxysilane, a methoxysilane, a di-ethoxysilane, a trichlorosilane, or a di-ethoxymethoxysilane.

8. The method of claim 1, wherein the silane functionalizing agent comprises a biotinylated silane.

9. The method of claim 1, further comprising:

contacting the substrate with a molecule of interest that binds the coupling moiety, thereby coupling the molecule of interest to the second surface portion.

10. The method of claim 9, wherein the molecule of interest comprises a biomolecule.

11. The method of claim 10, wherein the biomolecule is a polypeptide.

12. The method of claim 11, wherein the polypeptide is a protein or fragment thereof.

13. The method of claim 11, wherein the polypeptide is a substrate for a polypeptide sequencing reaction.

14. The method of claim 1, wherein the second silane composition comprises at least one chlorosilane in vapor phase.

15. The method of claim 1, further comprising, prior to (a) and (b):

treating the substrate with a phosphoryl halide in vapor phase, wherein the phosphoryl halide preferentially forms the phosphorus-containing layer on the first surface portion.

16. The method of claim 15, wherein the phosphoryl halide is an organic phosphoryl dihalide.

17. The method of claim 16, wherein the organic phosphoryl dihalide is an organic phosphoryl dichloride.

18. The method of claim 1, wherein the phosphorus-containing layer is an organophosphorus layer.

19. The method of claim 18, wherein the organophosphorus layer is an organophosphonate layer.

20. The method of claim 1, wherein at least a portion of the silane coating layer is formed on the phosphorus-containing layer.

21. The method of claim 1, wherein at least a portion of the silane coating layer is formed on the functionalized second surface portion.

* * * * *